United States Patent
Kim et al.

(10) Patent No.: US 11,628,203 B2
(45) Date of Patent: Apr. 18, 2023

(54) PHARMACEUTICAL COMPOSITION FOR TREATING RETINAL DYSTROPHIES, COMPRISING NKX3.2 AND FRAGMENT THEREOF AS ACTIVE INGREDIENTS

(71) Applicant: ICM CO., LTD., Seoul (KR)

(72) Inventors: Dae-Won Kim, Seoul (KR); Young-Na Yum, Goyang-si (KR); Heui-Young Ryu, Seoul (KR); Da-Un Jeong, Seoul (KR); Seung-Won Choi, Suwon-si (KR)

(73) Assignee: ICM CO., LTD., Seoul (KR)

( * ) Notice: Subject to any disclaimer, the term of this patent is extended or adjusted under 35 U.S.C. 154(b) by 0 days.

(21) Appl. No.: 17/273,546

(22) PCT Filed: Oct. 19, 2018

(86) PCT No.: PCT/KR2018/012428
§ 371 (c)(1),
(2) Date: Mar. 4, 2021

(87) PCT Pub. No.: WO2020/080583
PCT Pub. Date: Apr. 23, 2020

(65) Prior Publication Data
US 2021/0187065 A1 Jun. 24, 2021

(51) Int. Cl.
*A61K 38/17* (2006.01)
*A61P 27/02* (2006.01)

(52) U.S. Cl.
CPC .............. *A61K 38/17* (2013.01); *A61P 27/02* (2018.01)

(58) Field of Classification Search
None
See application file for complete search history.

(56) References Cited

U.S. PATENT DOCUMENTS

| 2004/0242482 A1* | 12/2004 | Gehring | G01N 33/6872 514/18.9 |
| 2010/0216660 A1* | 8/2010 | Nikolsky | C12Q 1/6886 506/17 |
| 2018/0236035 A1 | 8/2018 | Rosa | |

FOREIGN PATENT DOCUMENTS

| KR | 10-2011-0087462 A | | 8/2011 |
| KR | 20-2011-0087462 A | * | 8/2011 |
| KR | 10-2018-0118552 A | | 10/2018 |
| WO | 2011/093647 A2 | | 8/2011 |
| WO | 2012/097057 A2 | | 7/2012 |
| WO | WO 2012-097057 A2 | * | 7/2012 |
| WO | 2018/088813 A2 | | 5/2018 |
| WO | WO 2018-088813 A2 | * | 5/2018 |

OTHER PUBLICATIONS

GenBank:NP_001180.1,homeoboxproteinNkx-3.2[Homosapiens],Aug. 5, 2018.*
JamieL.Zagozewski, et al.,"Theroleofhomeoboxgenesinretinaldevelopmentanddisease", Developmental Biology ,2014, pp. 195-208,vol. 393.*
International Search Report for PCT/KR2018/012428 dated Jul. 15, 2019 (PCT/ISA/210).

* cited by examiner

*Primary Examiner* — Maury A Audet
(74) *Attorney, Agent, or Firm* — Sughrue Mion, PLLC

(57) ABSTRACT

A pharmaceutical composition contains Nkx3.2 and a fragment thereof as an active ingredient. The Nkx3.2 and/or the fragment thereof inhibit(s) retinal degeneration caused by oxidative stress and preserve(s) visual function. In addition, the Nkx3.2 and/or the fragment thereof inhibit(s) cell death due to the oxidative stress of retinal pigment epithelial cells and inhibit(s) choroidal neovascularization and retinal edema. Therefore, a composition containing the Nkx3.2 and/or the fragment thereof as active ingredient(s) can be effectively used for preventing or treating retinal dystrophies or macular degeneration.

5 Claims, 25 Drawing Sheets
Specification includes a Sequence Listing.

[FIG. 1]
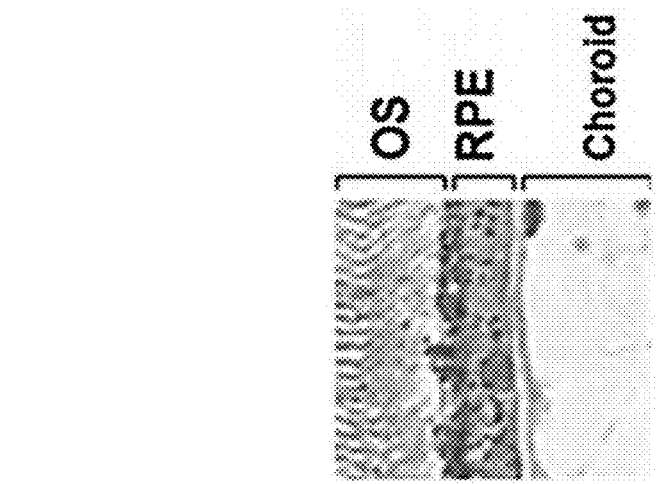
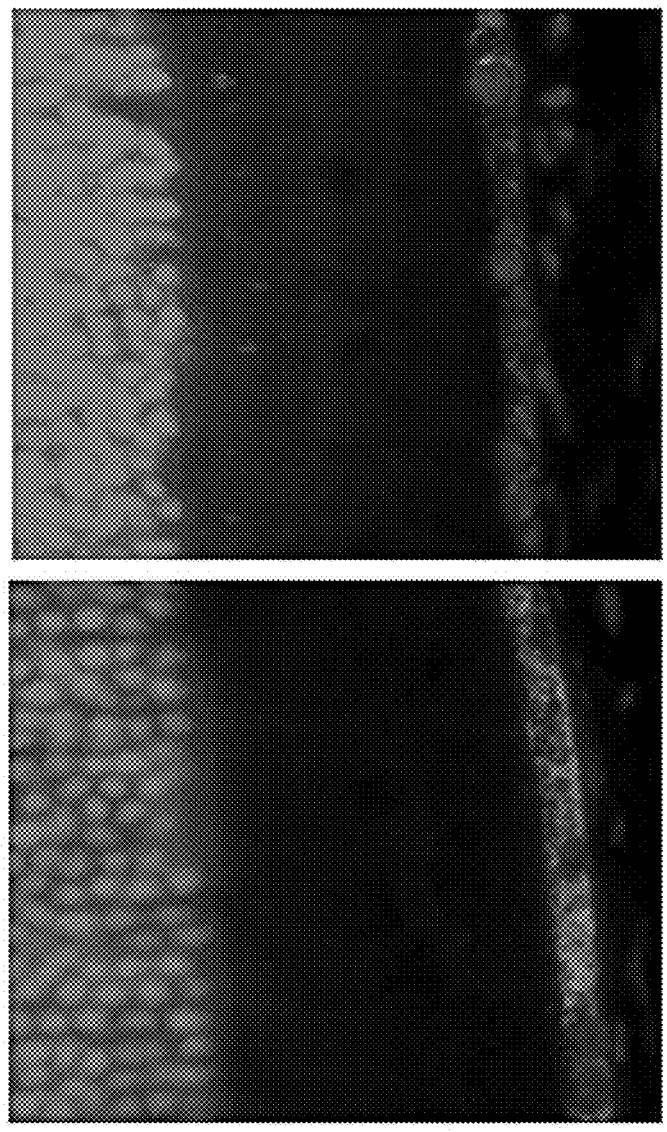

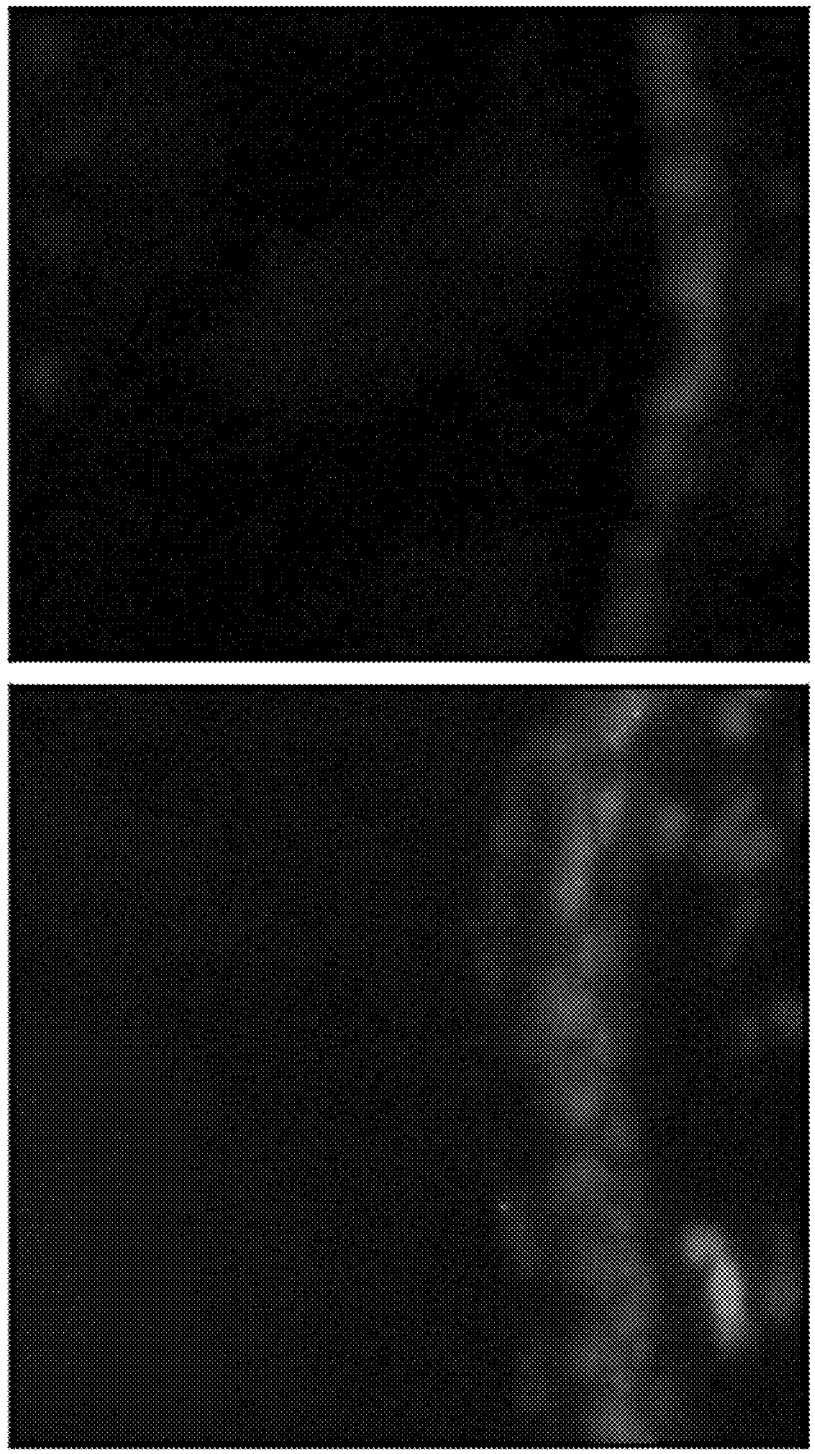
[FIG. 2]

[FIG. 3]
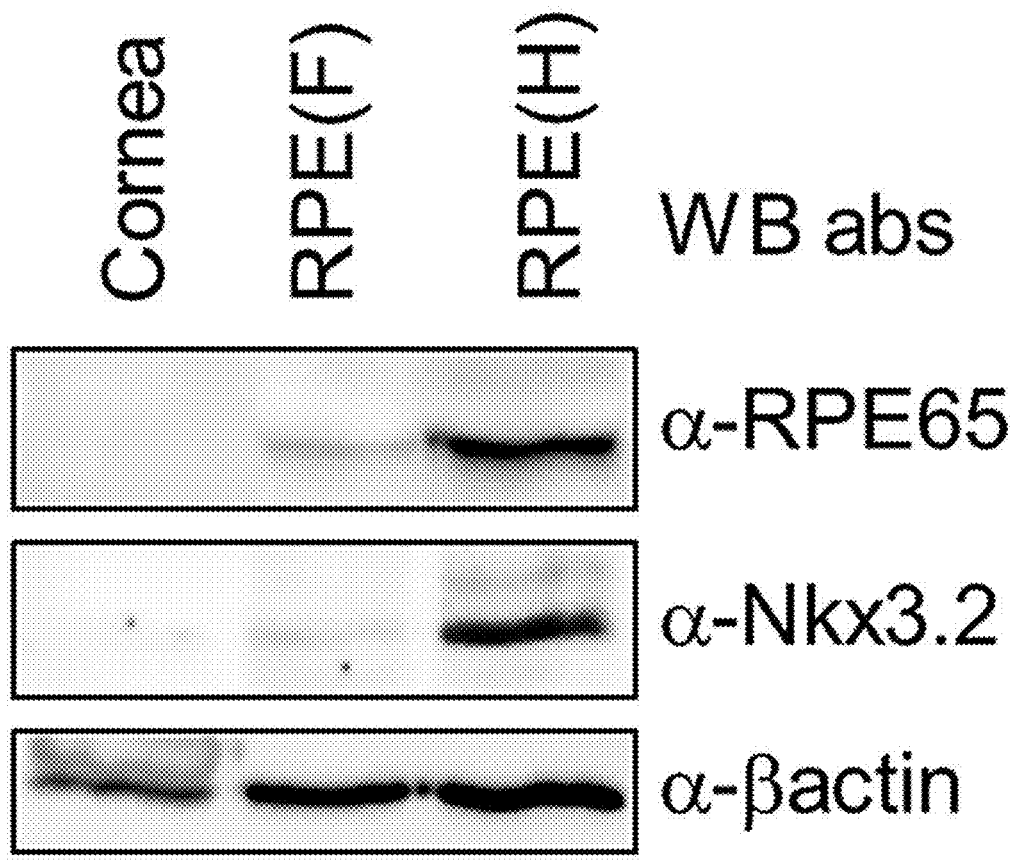

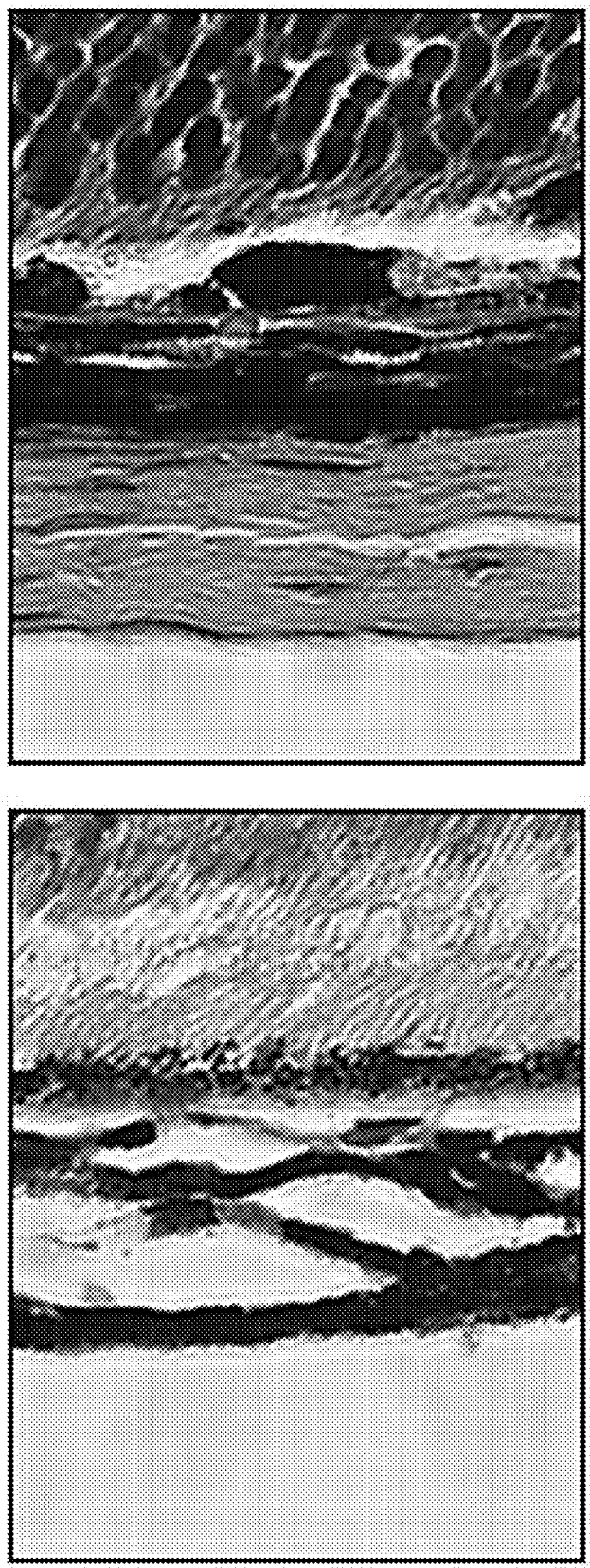
[FIG. 4]

[FIG. 5]
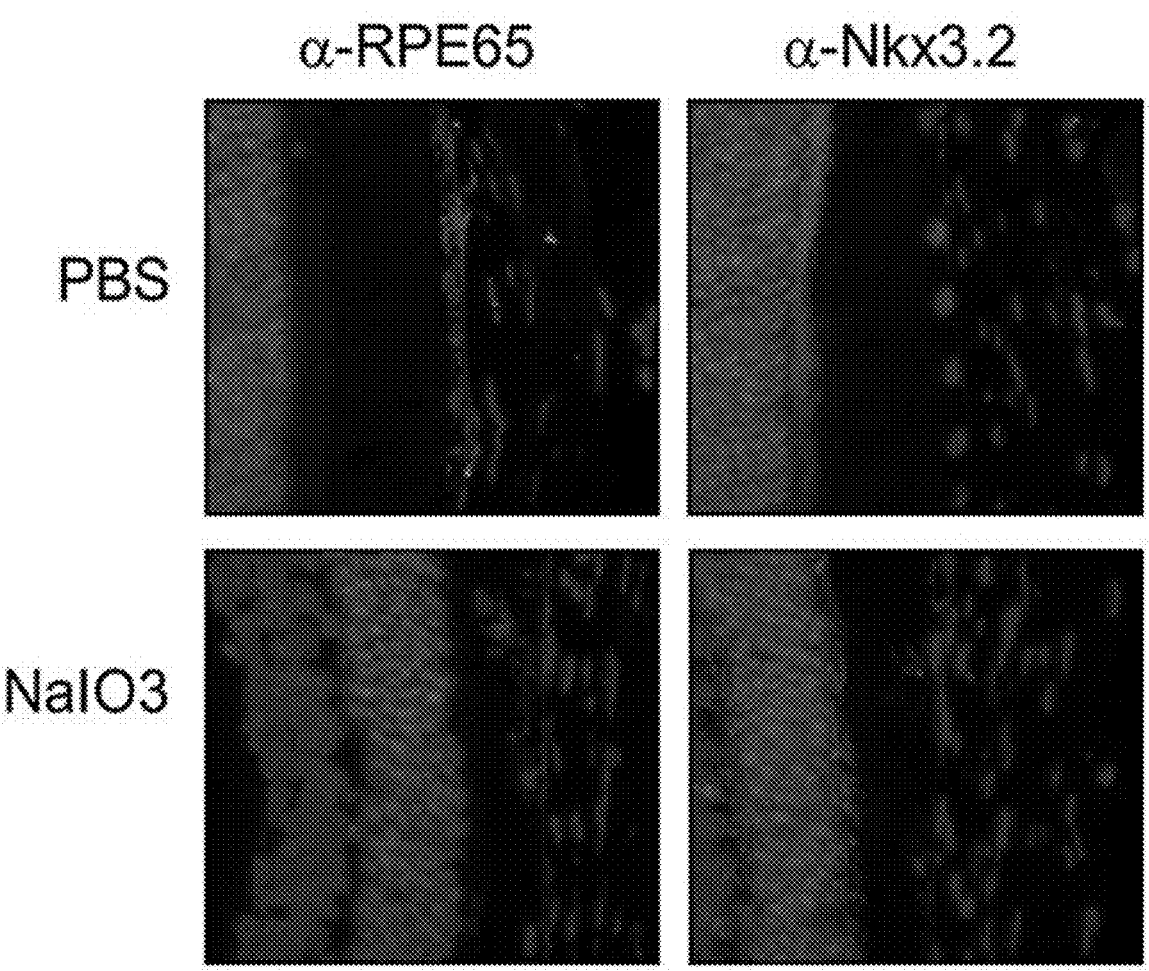

[FIG. 6]
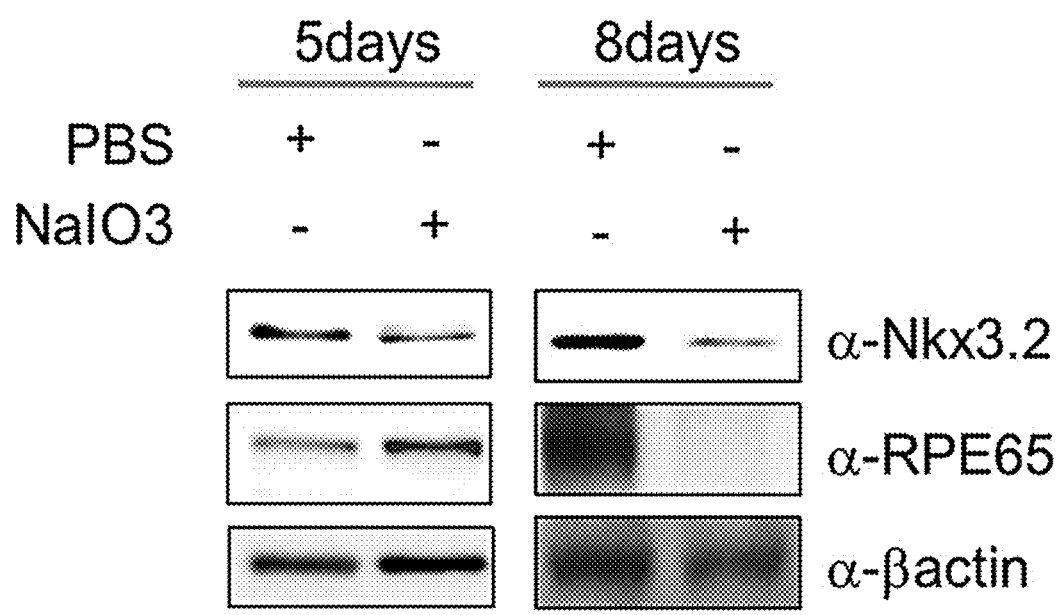

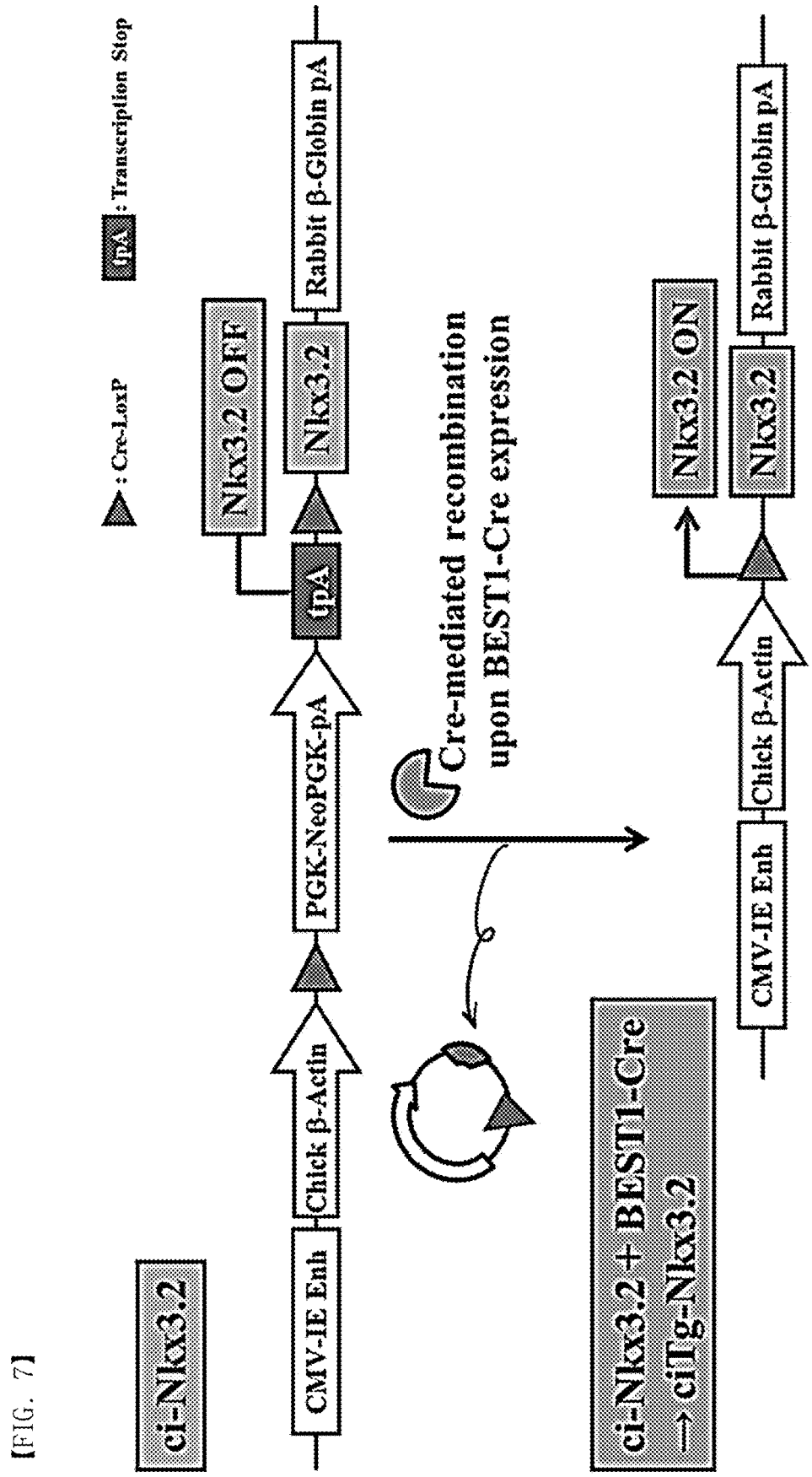
[FIG. 7]

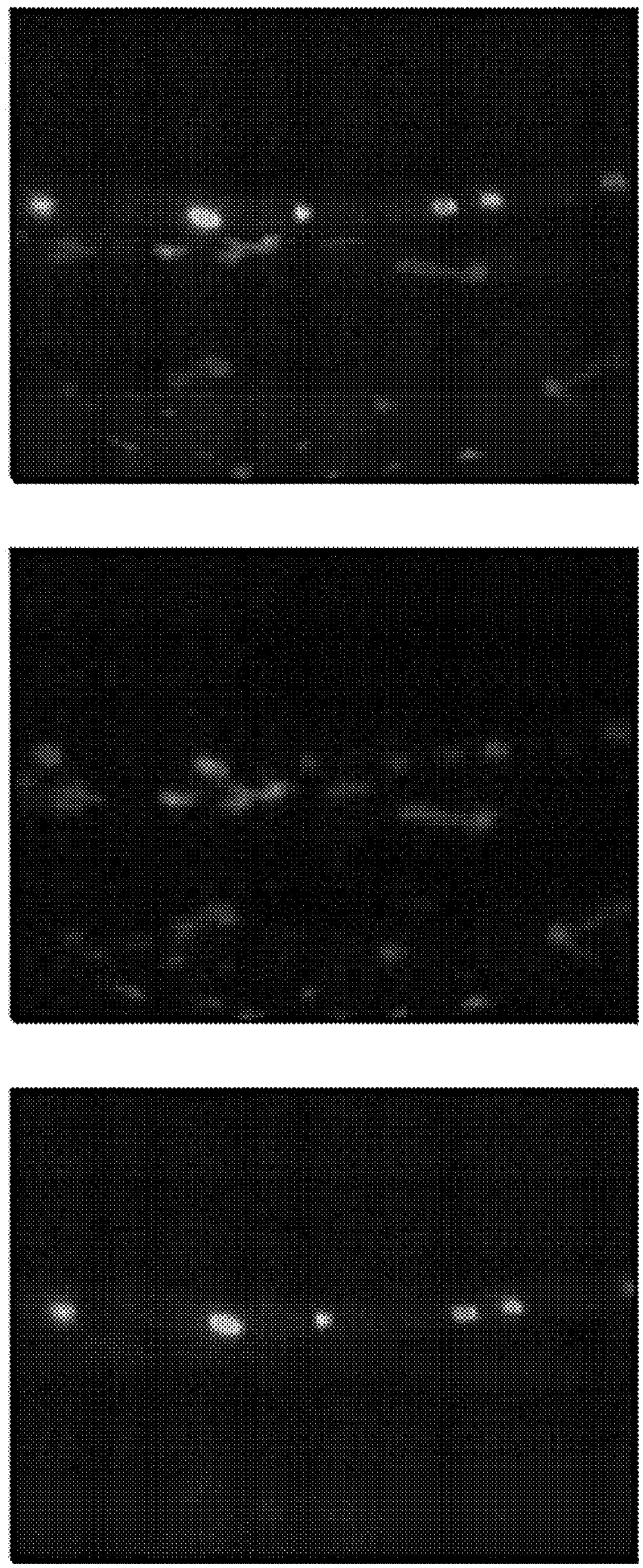
[FIG. 8]

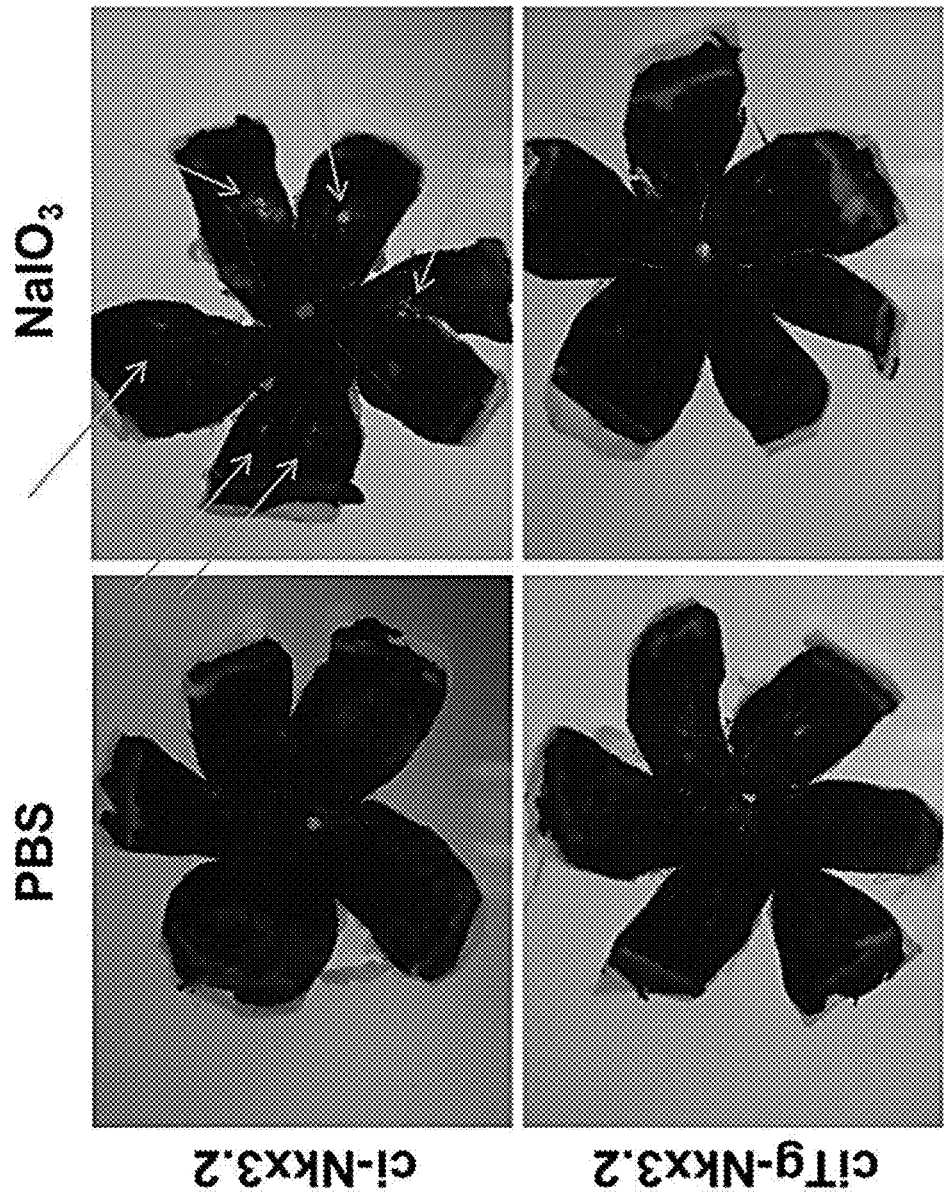
[FIG. 9]

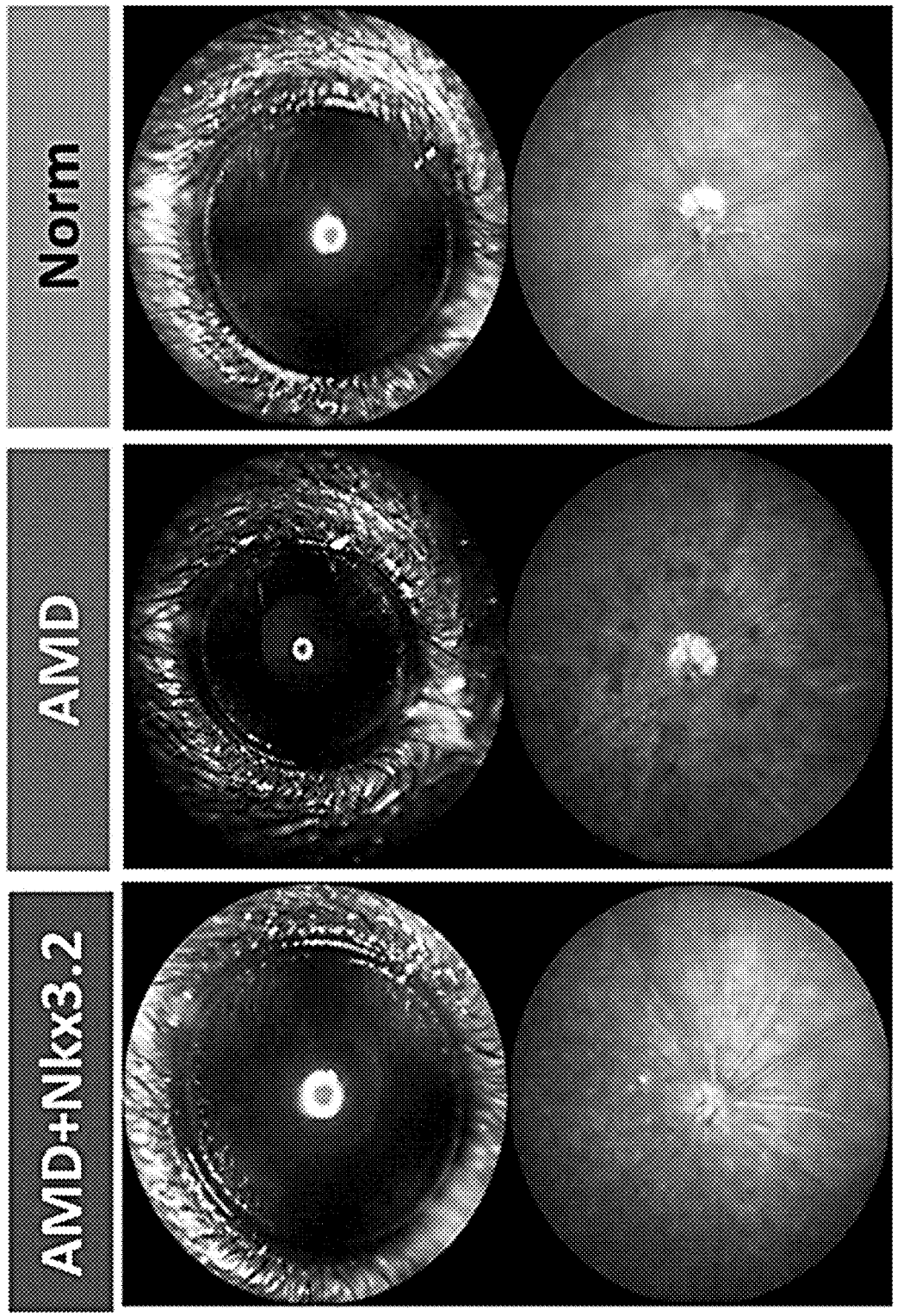
[FIG. 10]

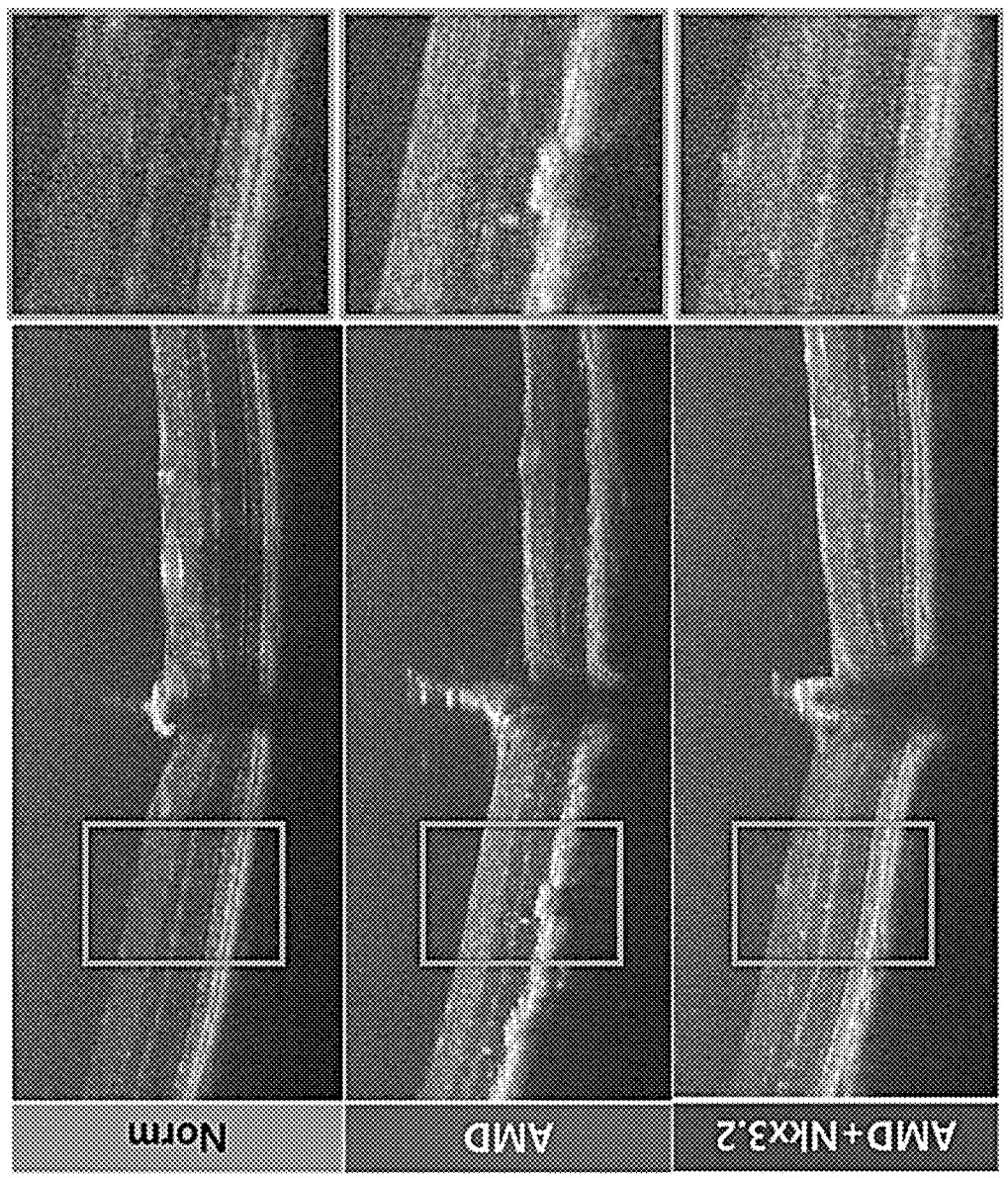
[FIG. 11]

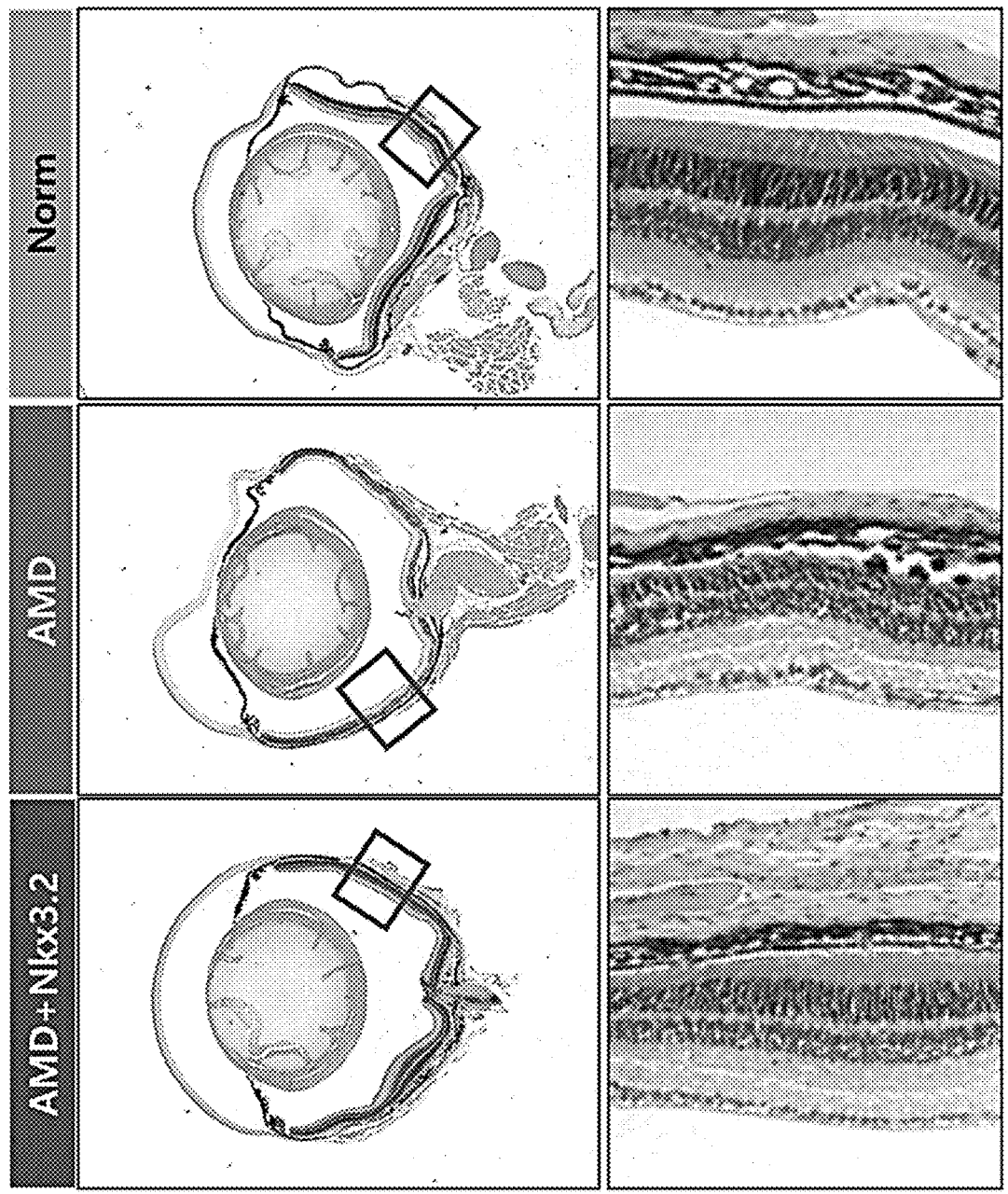
[FIG. 12]

[FIG. 13]
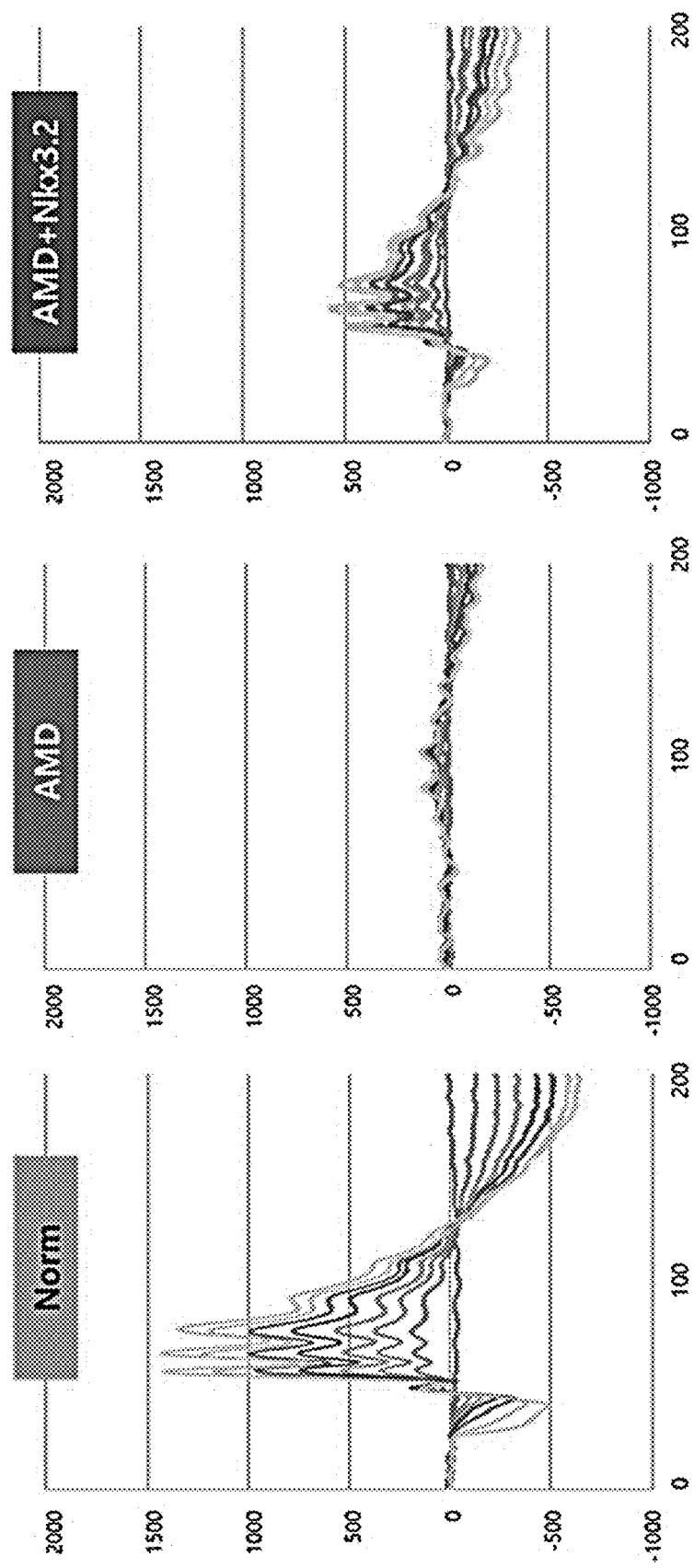

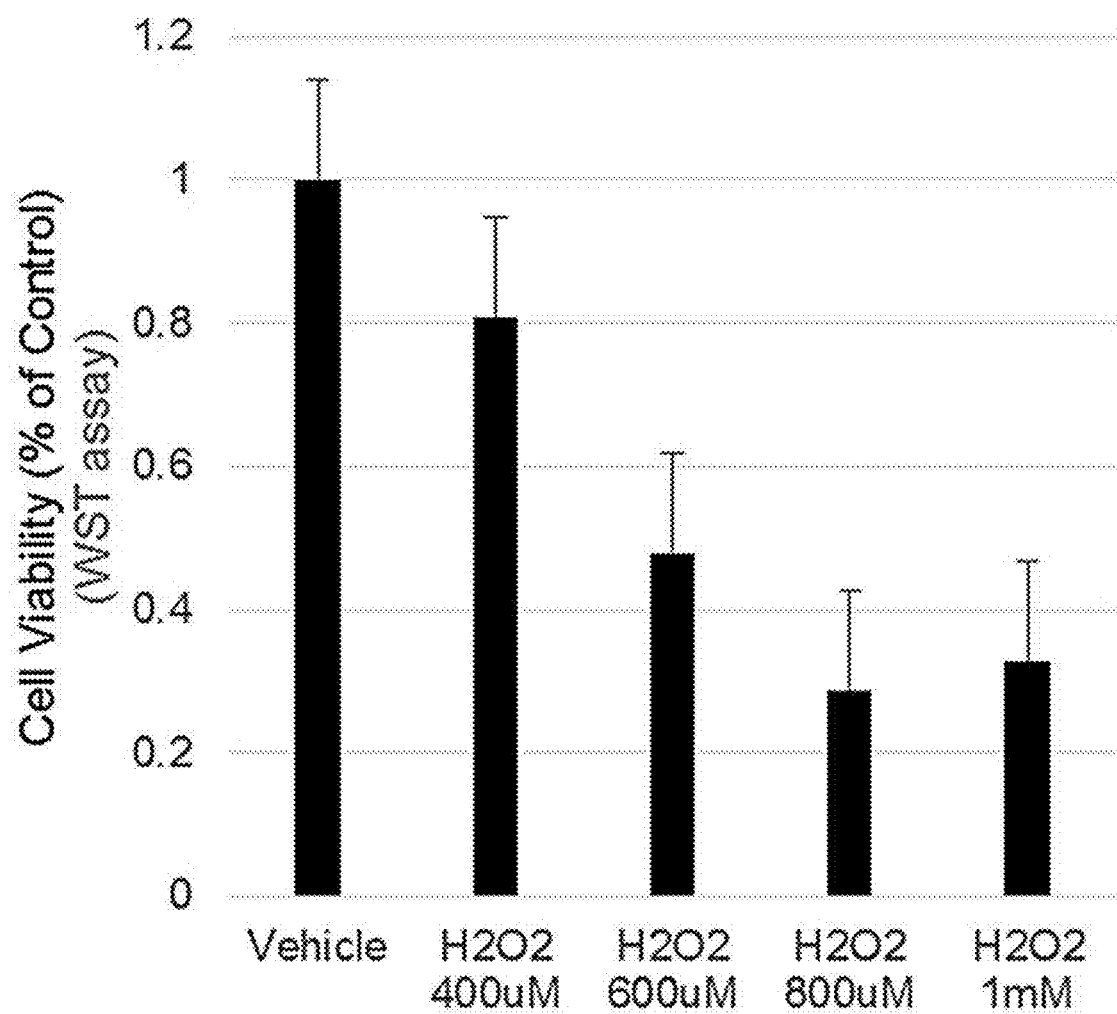
[FIG. 14]

[FIG. 15]
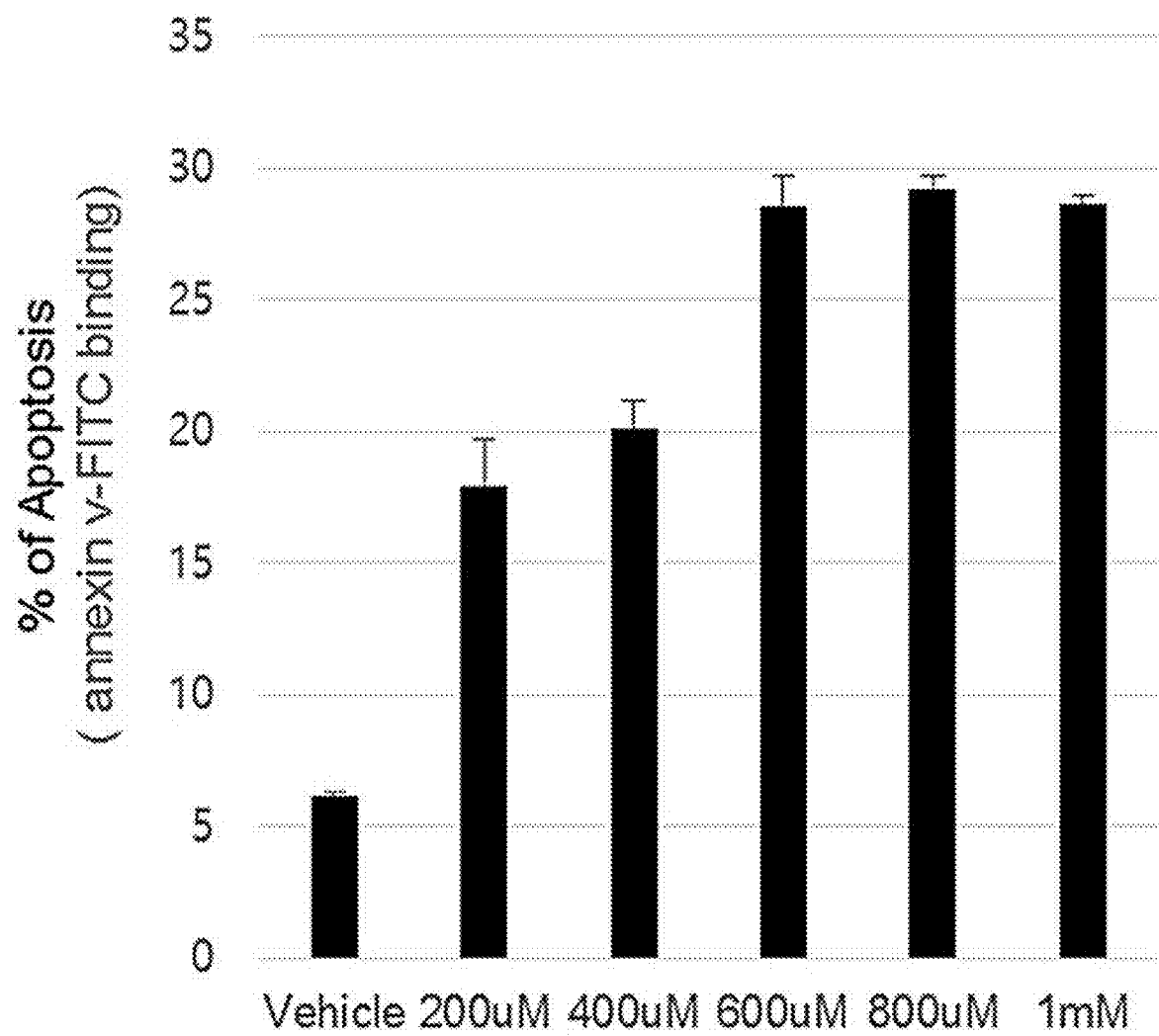

[FIG. 16]
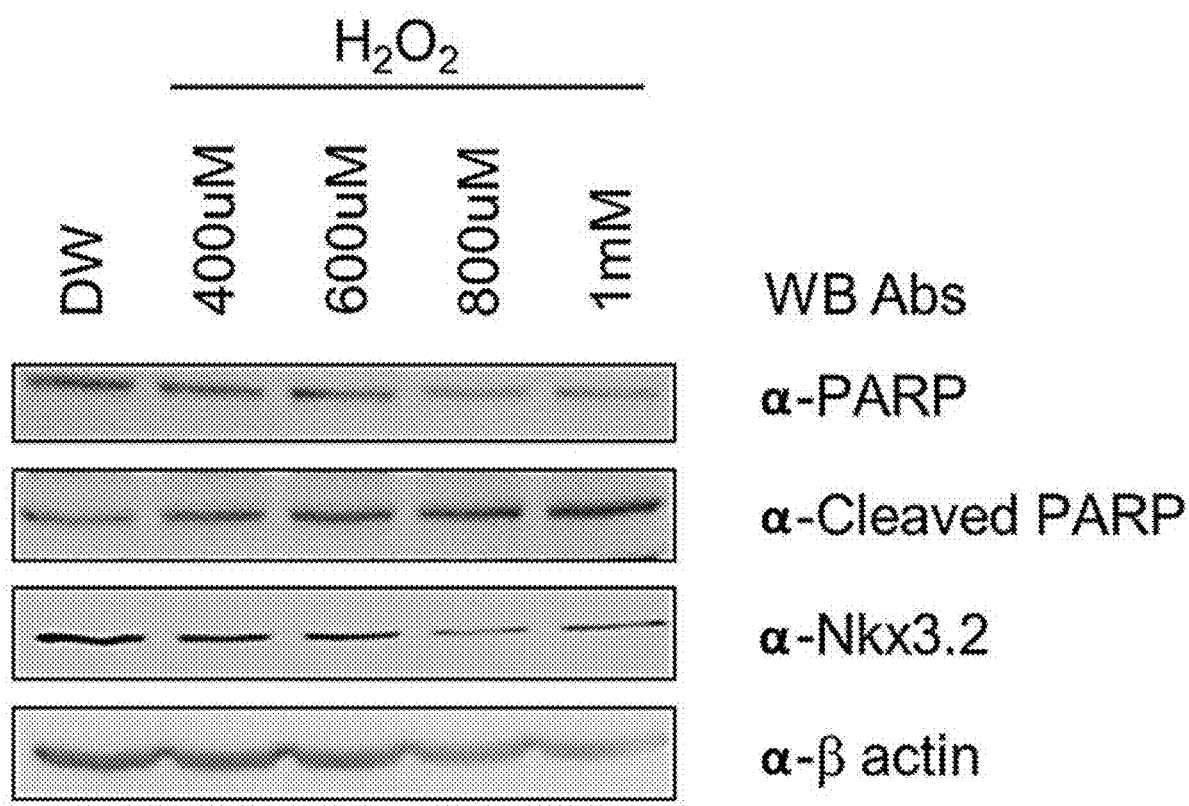

[FIG. 17]
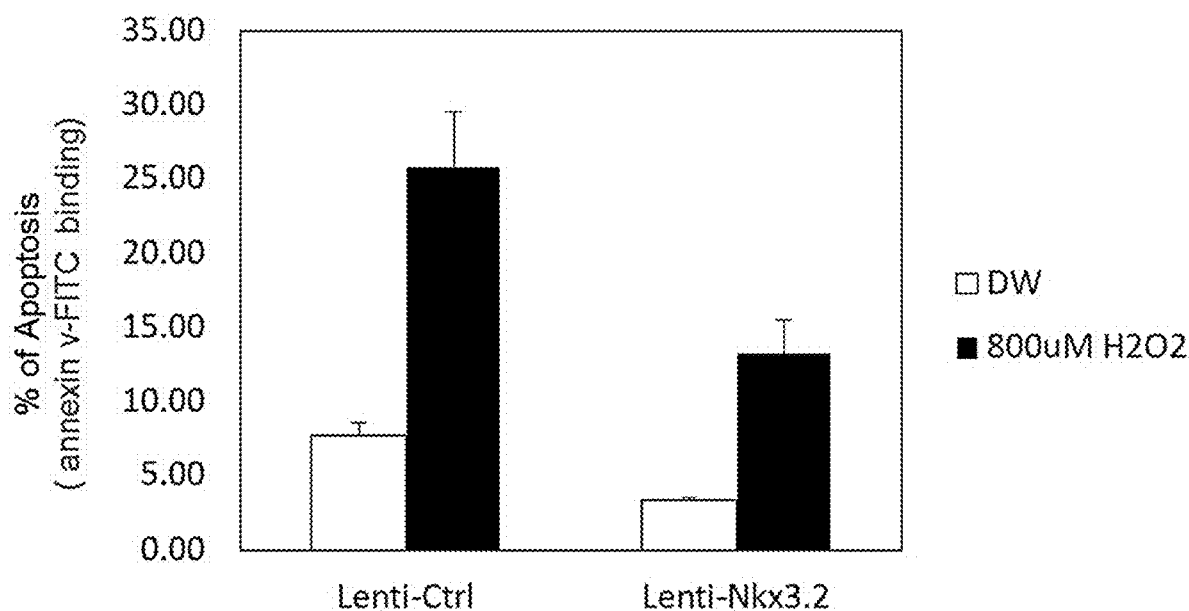
[FIG. 18]
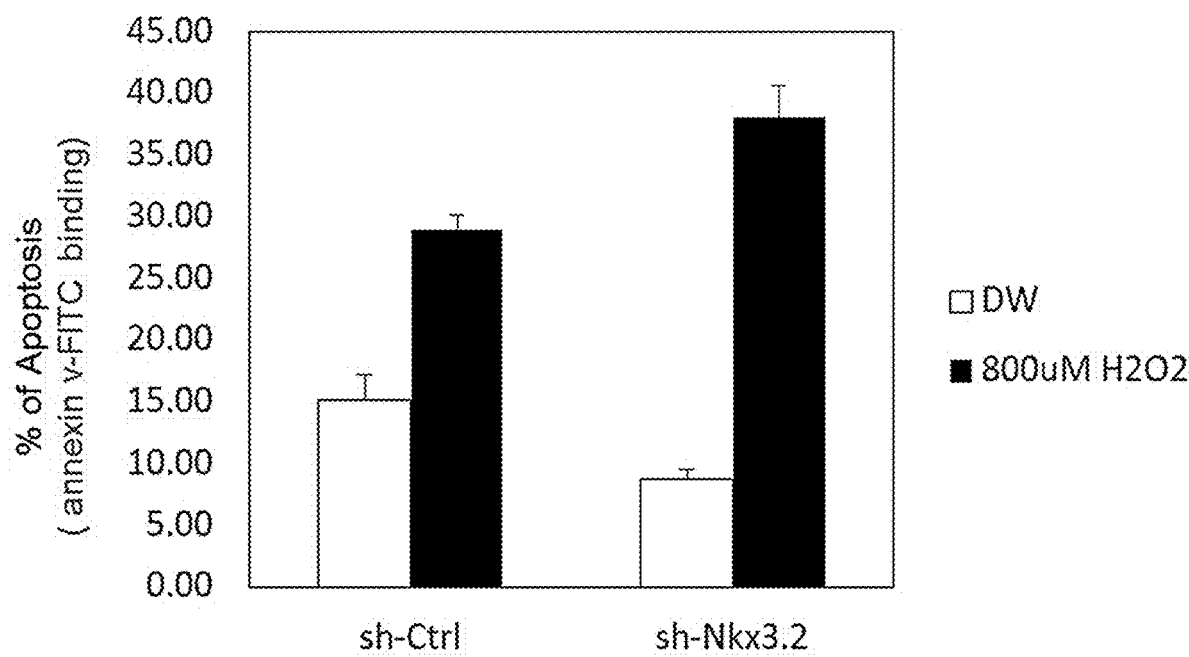

[FIG. 19]
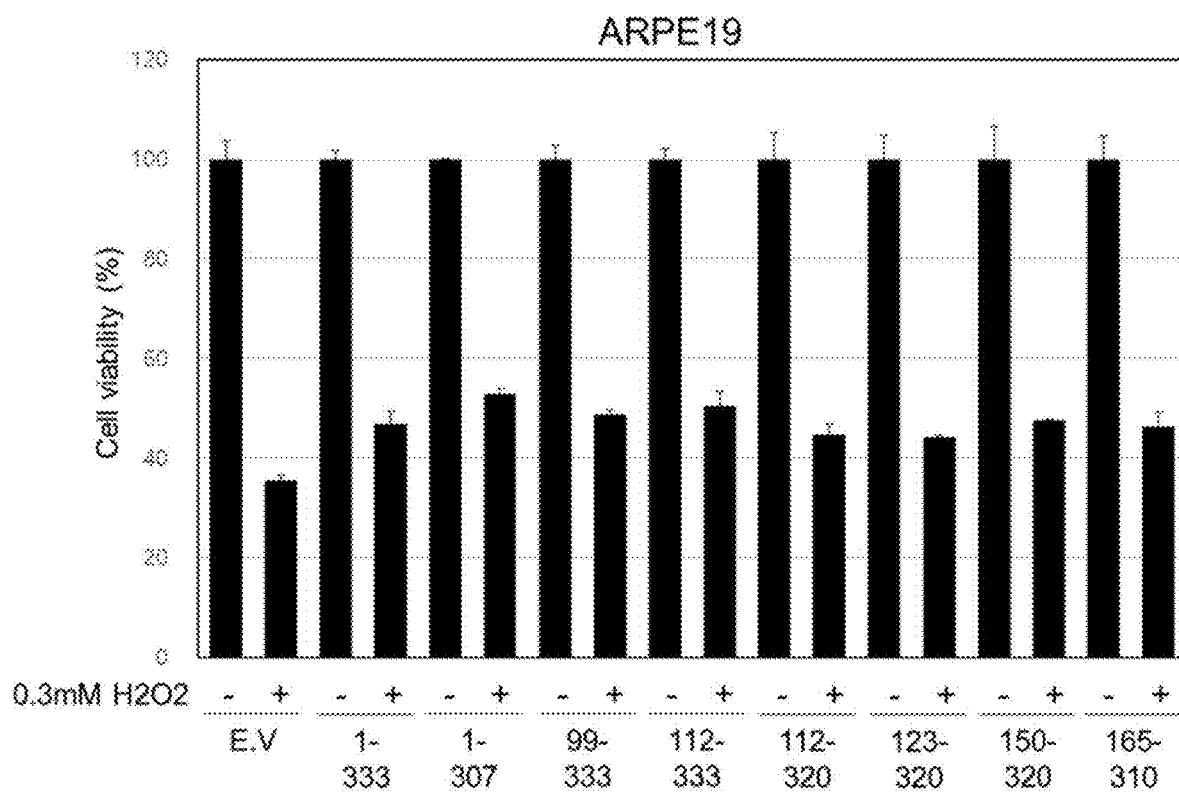

[FIG. 20a]
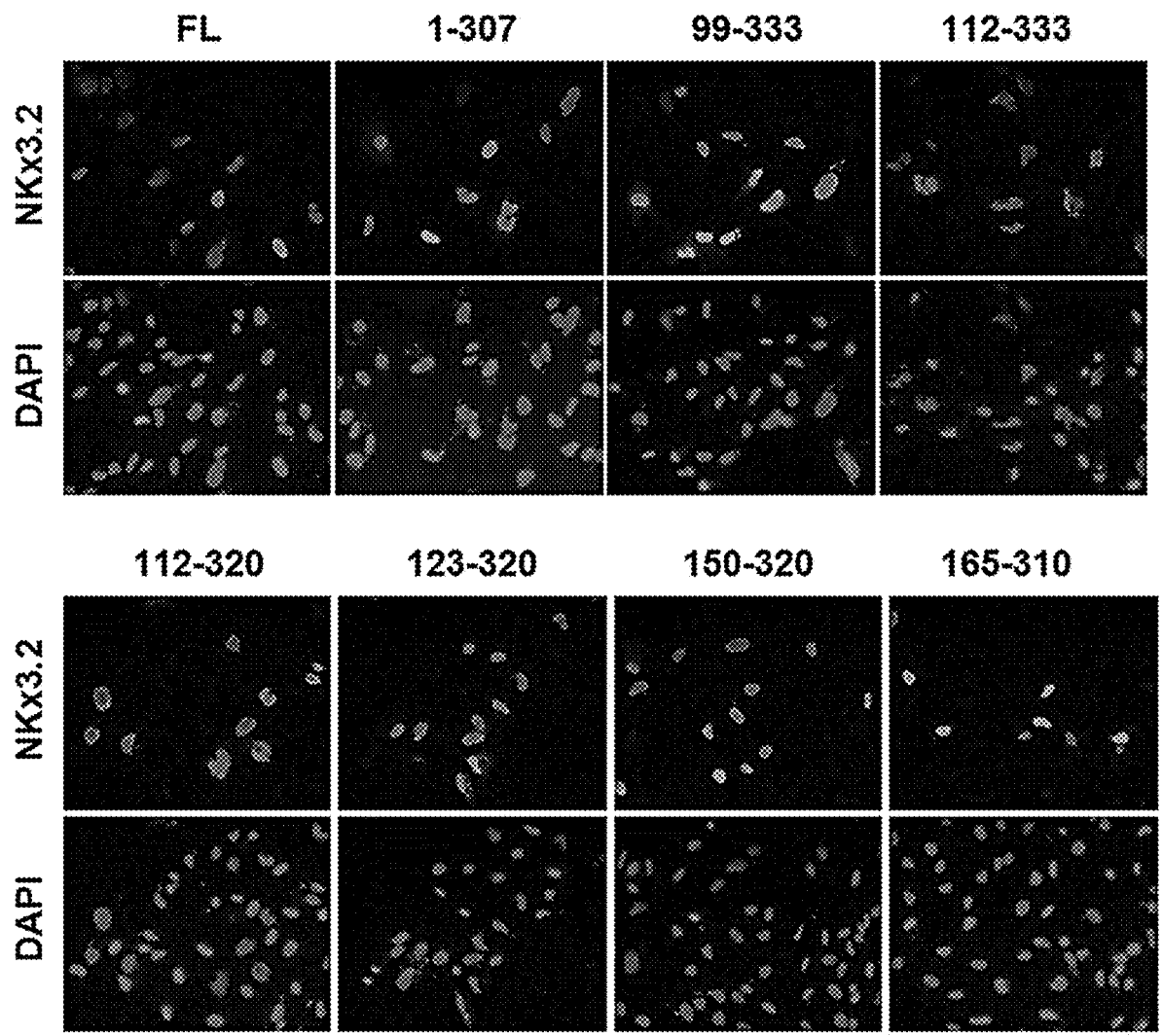

[FIG. 20b]

| Sample | FL 13O7 DAPI | FITC | 99-333 DAPI | FITC | 172-333 DAPI | FITC | 172-320 DAPI | FITC | 123-320 DAPI | FITC | 150-320 DAPI | FITC | 165-310 DAPI | FITC |
|---|---|---|---|---|---|---|---|---|---|---|---|---|---|---|
| 1 | 43 | 6 | 36 | 10 | 24 | 11 | 35 | 11 | 31 | 10 | 34 | 8 | 38 | 11 | 62 | 6 |
| 2 | 28 | 6 | 51 | 7 | 15 | 8 | 31 | 9 | 30 | 8 | 26 | 7 | 40 | 11 | 55 | 5 |
| 3 | 34 | 6 | 43 | 14 | 35 | 13 | 24 | 9 | 34 | 11 | 37 | 9 | 27 | 6 | 53 | 12 |
| 4 | 35 | 7 | 32 | 8 | 24 | 9 | 35 | 12 | 32 | 11 | 40 | 8 | 41 | 9 | 55 | 9 |
| 5 | 42 | 16 | 58 | 14 | 27 | 6 | 33 | 11 | 43 | 10 | 29 | 8 | 27 | 7 | 57 | 9 |
| 6 | 52 | 7 | 37 | 15 | 28 | 10 | 33 | 9 | 62 | 11 | 54 | 9 | 39 | 8 | 39 | 7 |
| 7 | 42 | 12 | 35 | 5 | 33 | 9 | 43 | 12 | 41 | 7 | 27 | 13 | 34 | 7 | 56 | 6 |
| 8 | 17 | 12 | 66 | 9 | 27 | 7 | 28 | 8 | 24 | 8 | 38 | 13 | 21 | 8 | 39 | 5 |
| 9 | 26 | 5 | 39 | 11 | 38 | 11 | 24 | 7 | 38 | 16 | 55 | 17 | 36 | 13 | 39 | 13 |
| 10 | 15 | 3 | 48 | 10 | 37 | 11 | 37 | 11 | 49 | 7 | 47 | 8 | 56 | 12 | 52 | 5 |
| Average | 33.4 | 8 | 44.5 | 10.3 | 28.8 | 8.9 | 32.3 | 9.9 | 38.4 | 9.9 | 38.7 | 10 | 35.9 | 9.2 | 50.7 | 7.7 |
| FITC/DAPI | 0.239520958 | | 0.231460674 | | 0.309027778 | | 0.306501548 | | 0.2578125 | | 0.258397933 | | 0.256267409 | | 0.151873767 | |
| FITC/DAPI(%) | 25% | | 23% | | 31% | | 31% | | 26% | | 26% | | 26% | | 15% | |

[FIG. 20c]
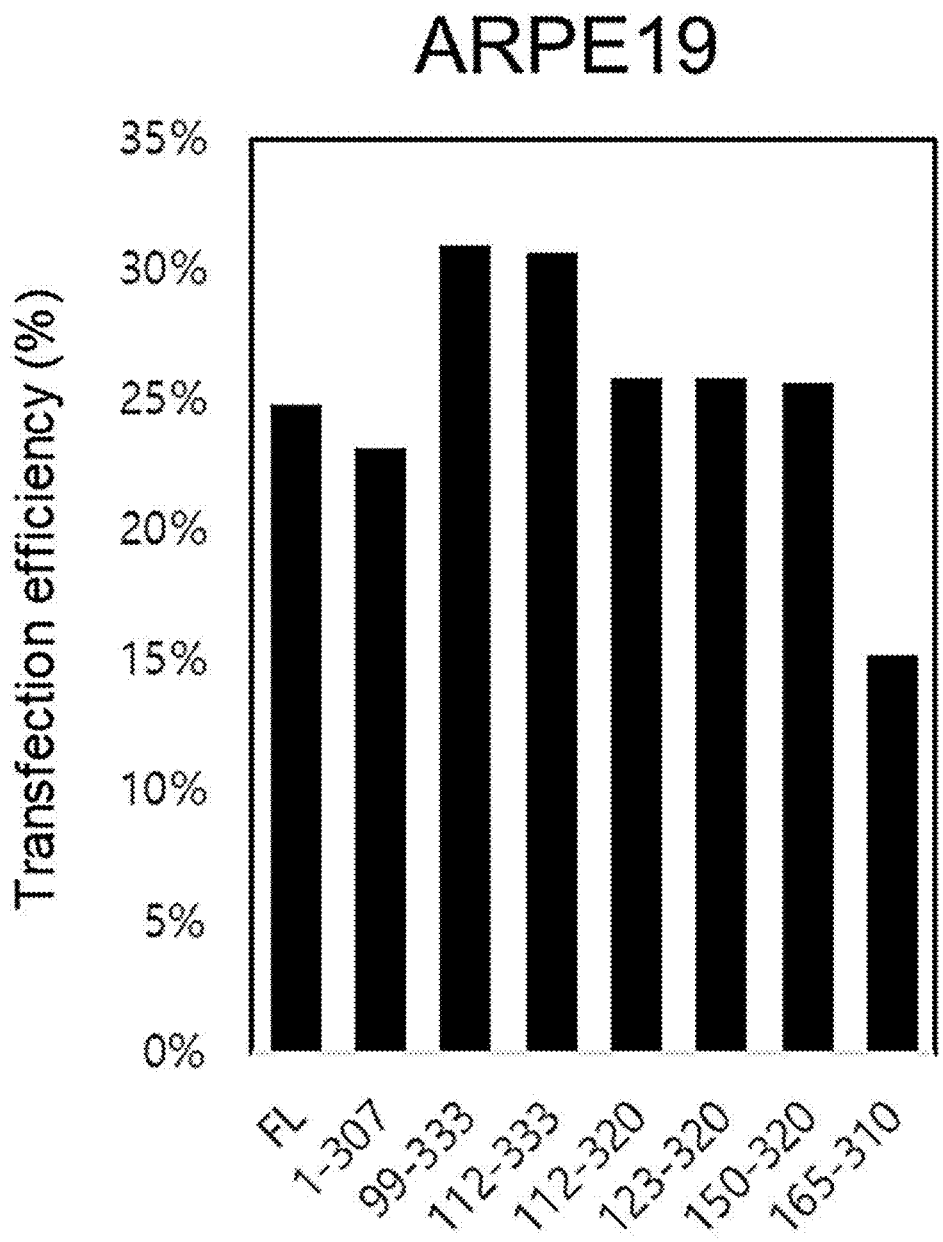

[FIG. 21a]
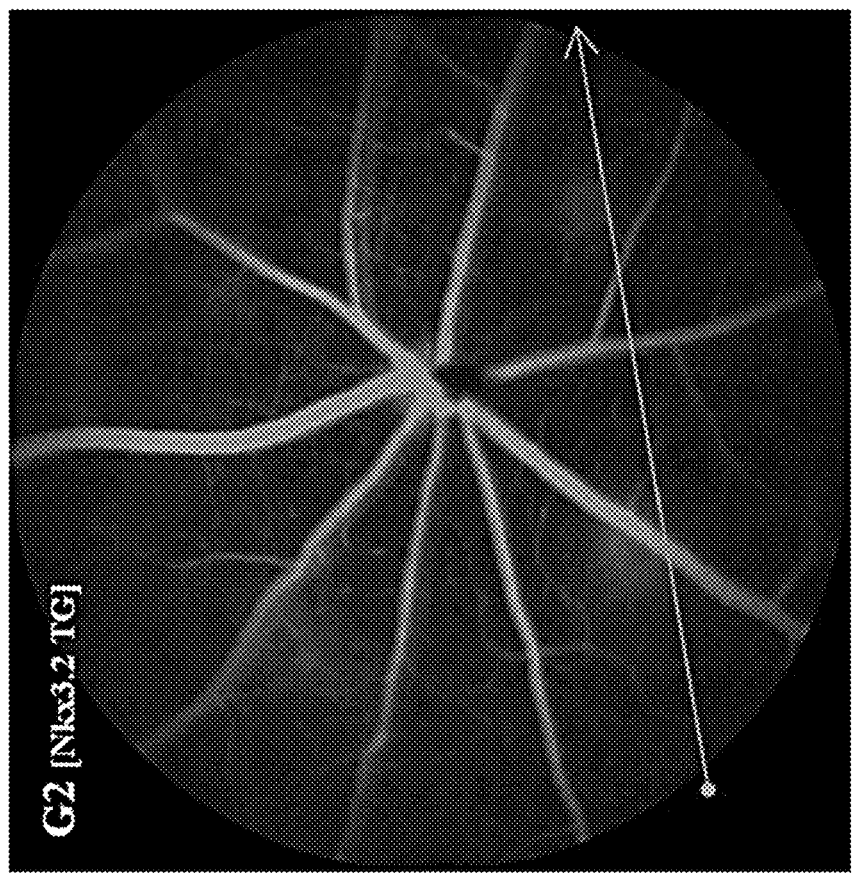
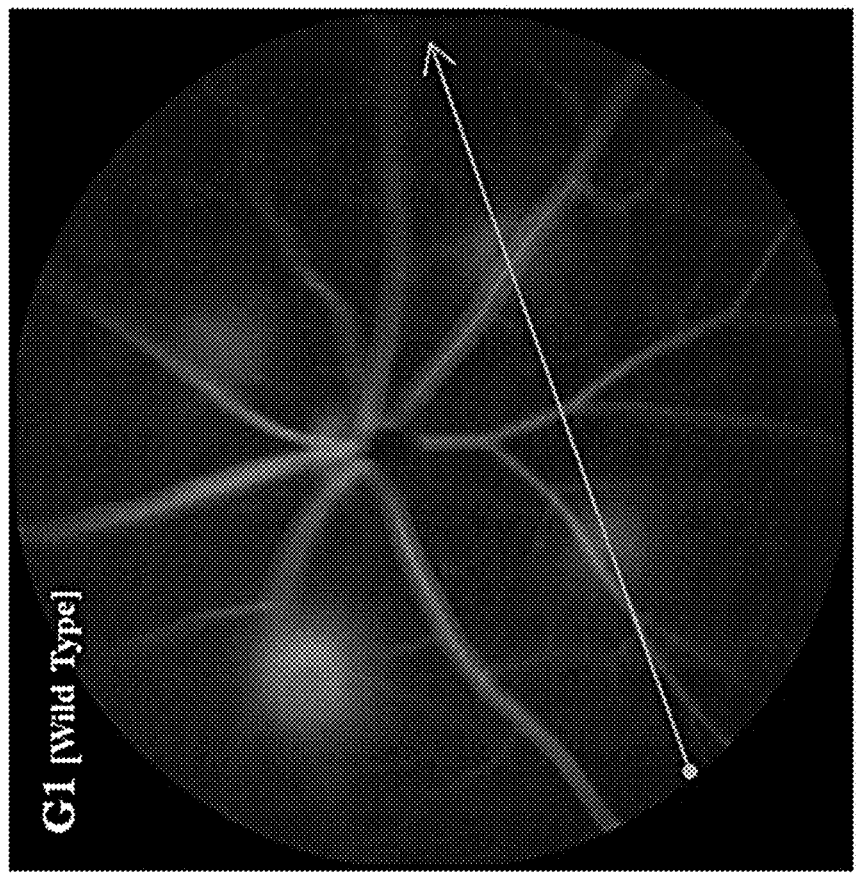

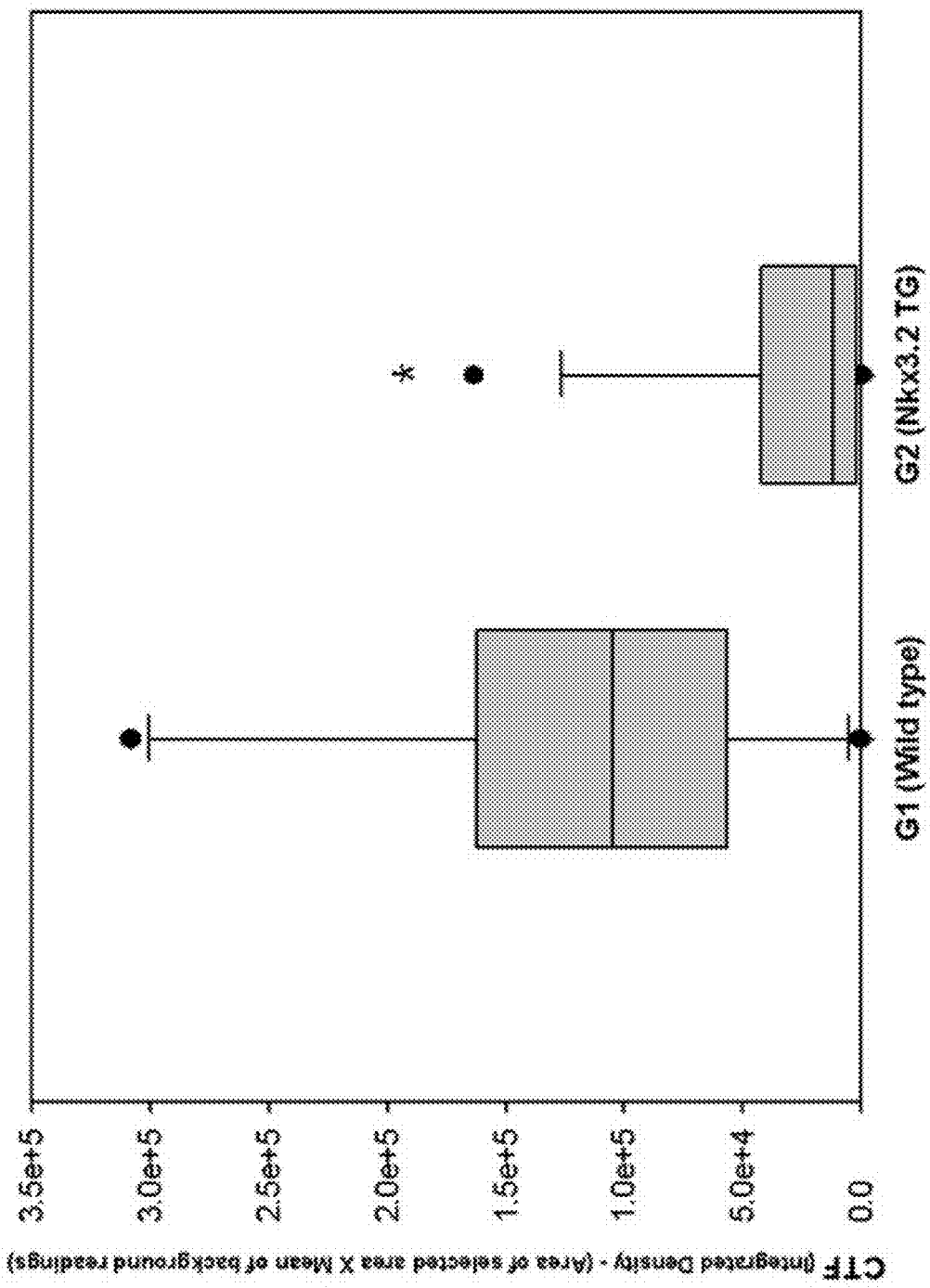
[FIG. 21b]

[FIG. 22a]
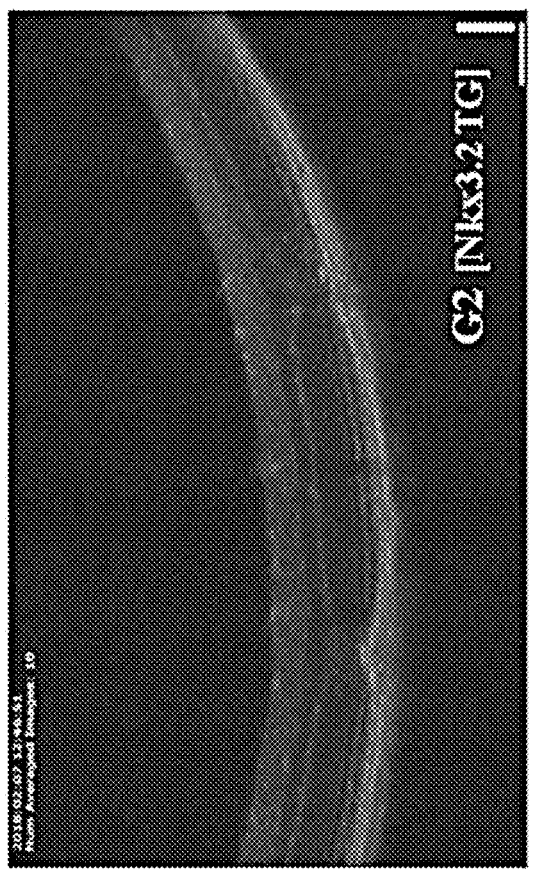
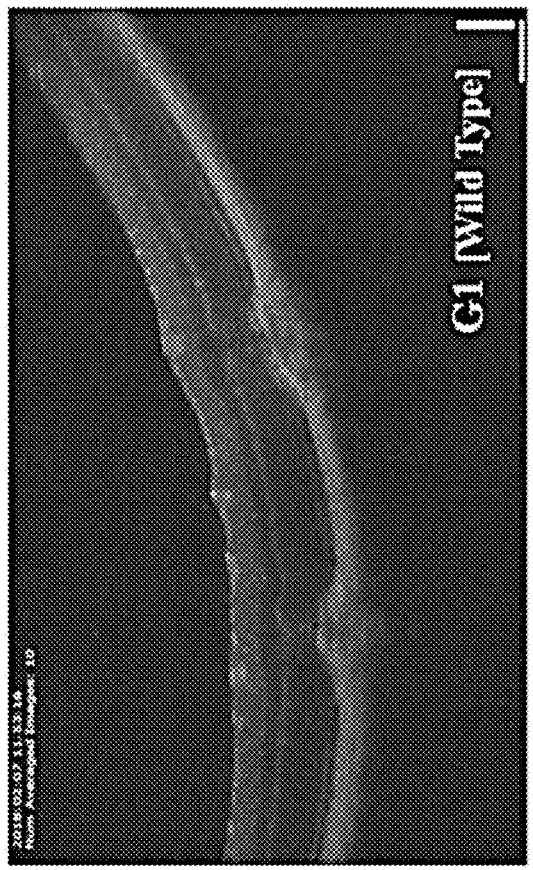

[FIG. 22b]
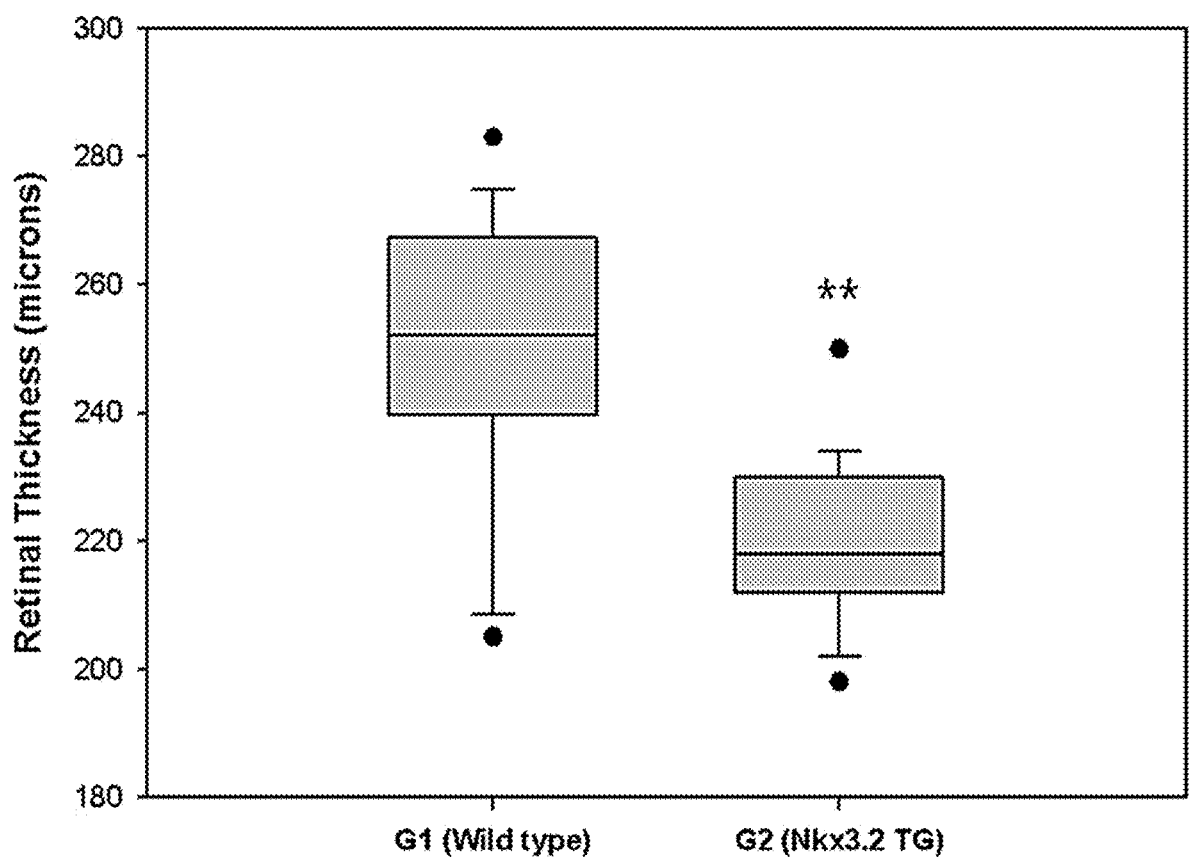

PHARMACEUTICAL COMPOSITION FOR TREATING RETINAL DYSTROPHIES, COMPRISING NKX3.2 AND FRAGMENT THEREOF AS ACTIVE INGREDIENTS

CROSS REFERENCE TO RELATED APPLICATIONS

This application is a National Stage of International Application No. PCT/KR2018/012428 filed Oct. 19, 2018.

SEQUENCE LISTING

The content of the electronically submitted sequence listing, file name: Sequence_Listing_As_Filed.txt; size: 44,118 bytes; and date of creation: Feb. 22, 2021, filed herewith, is incorporated herein by reference in its entirety.

TECHNICAL FIELD

The present invention relates to a pharmaceutical composition for preventing or treating retinal diseases, comprising Nkx3.2 and/or a fragment thereof as active ingredients.

BACKGROUND ART

As our society enters an aging society, interest in age-related diseases and treatments thereof is increasing. Among various senile diseases, macular degeneration, which is a representative senile eye disease, is a disease in which vision impairment is caused by degeneration in the macula located in the center of the retina inside the eye.

In macular degeneration, decreased vision or vision loss occurs due to decreased macular function caused by physical aging. This disease is a major cause of vision loss with age. Macular degeneration is a disease that usually occurs in the 50s and 60s, and may rarely occur in younger age groups. The disease is known to be caused by physical aging, cardiovascular disease, smoking, high level of blood cholesterol, environmental pollution, exposure to sunlight, or the like.

There are two types of macular degeneration: dry macular degeneration and wet macular degeneration. Dry macular degeneration occurs in a case where a type of aging-related deposit called drusen, is generated in the retina, or a lesion such as retinal pigment epithelial atrophy develops. About 90% of patients suffering from macular degeneration have dry macular degeneration. In dry macular degeneration, visual cells in the macula slowly undergo atrophy, and thus result in gradually decreased vision over time. Although dry macular degeneration does not cause severe vision loss, it may develop into a wet type. For wet macular degeneration, new blood vessels are abnormally formed in the choroid, and thus severe visual damage is likely to occur due to these blood vessels themselves, or bleeding, effusion, or the like therefrom. Wet macular degeneration may lead to blindness due to disc-like atrophy, severe bleeding, or the like within months to years after onset (Oh, M. J. & Lee, S. Y., 2012).

On the other hand, in a case where visual impairment begins due to macular degeneration, recovery to the previous vision cannot be achieved. Thus, it is important to detect and treat the macular degeneration at an early stage. Macular degeneration can be detected at an early stage in a case of using the Amsler Grid that is a self-assessment test for macular degeneration. As such, regarding macular degeneration, early detection and treatment thereof can minimize vision loss; however, there are currently no reliable treatments.

DISCLOSURE OF INVENTION

Technical Problem

While studying therapeutic agents for macular degeneration, the present inventors have found that Nkx3.2 and/or a fragment thereof has an excellent effect on prevention or treatment of retinal dystrophies, such as inhibition of retinal pigment epithelial cell death and retinal degeneration, which are caused by oxidative stress, preservation of visual function, and inhibition of choroidal neovascularization and retinal edema. Based on this finding, the present inventors have completed the present invention.

An object of the present invention is to provide a pharmaceutical composition for preventing or treating retinal dystrophies, comprising, as an active ingredient, Nkx3.2 and/or a fragment thereof.

Solution to Problem

To achieve the above object, the present invention provides a pharmaceutical composition for preventing or treating retinal dystrophies, comprising, as an active ingredient, Nkx3.2 or a fragment thereof.

In addition, the present invention provides the pharmaceutical composition for preventing or treating retinal dystrophies, in which the Nkx3.2 fragment is a polypeptide represented by Formula (I):

N-terminal extension domain-core domain-C-terminal extension domain    (I)

In Formula (I), the core domain is a polypeptide having the amino acid sequence of SEQ ID NO: 1;

the N-terminal extension domain is a polypeptide having the amino acid sequence of SEQ ID NO: 3, in which 1 to 42 amino acids may be consecutively deleted from the N-terminus to the C-terminus direction, starting from the amino acid at position 1 of SEQ ID NO: 3; and the C-terminal extension domain is a polypeptide having the amino acid sequence of SEQ ID NO: 5, in which 1 to 23 amino acids may be consecutively deleted from the C-terminus to the N-terminus direction, starting from the amino acid at position 24 of SEQ ID NO: 5.

In addition, the present invention provides a method for preventing or treating retinal dystrophies, comprising a step of administering a polypeptide to an individual, in which the polypeptide is the Nkx3.2 and/or a fragment thereof.

Effects of Invention

The Nkx3.2 and/or a fragment thereof according to the present invention inhibits retinal degeneration caused by oxidative stress and preserves visual function. In addition, the Nkx3.2 and/or a fragment thereof inhibits retinal pigment epithelial cell death caused by oxidative stress, and inhibits choroidal neovascularization and retinal edema. Therefore, a composition comprising, as an active ingredient, the Nkx3.2 and/or a fragment thereof can be effectively used in prevention or treatment of retinal dystrophies.

BRIEF DESCRIPTION OF DRAWINGS

FIG. 1 illustrates expression of Nkx3.2 protein in retinal pigment epithelial cells of C57BL/6 mice, detected through immunohistochemical staining Here, OS is an abbreviation for outer segment.

FIG. 2 illustrates expression of Nkx3.2 protein in human retinal pigment epithelial cells, detected through immunohistochemical staining.

FIG. 3 illustrates expression of Nkx3.2 protein in human retinal pigment epithelial cells, detected through Western blot analysis. Here, WB abs is an abbreviation for Western blot antibodies.

FIG. 4 illustrates retinal pigment epithelial lesions in a retinal degeneration mouse model, the lesions having been caused by oxidative stress.

FIG. 5 illustrates expression of Nkx3.2 protein in a retinal degeneration mouse model, detected through immunohistochemical staining.

FIG. 6 illustrates expression of Nkx3.2 protein in a retinal degeneration mouse model, detected through Western blot analysis.

FIG. 7 illustrates a schematic diagram of a method for producing a mouse in which Nkx3.2 is overexpressed specifically in retinal pigment epithelial cells. The abbreviations illustrated in FIG. 7 have the following meanings: ci-Nkx3.2=Cre-inducible Nkx3.2; ciTg-Nkx3.2=Cre-inducible Nkx3.2 transgenic; and tpA=Transcription Stop.

FIG. 8 illustrates expression of Nkx3.2 protein in the retinal pigment epithelium of mice, in which Nkx3.2 is overexpressed specifically in retinal pigment epithelial cells, detected through immunohistochemical staining.

FIG. 9 illustrates degree of retinal degeneration depending on the expression level of Nkx3.2 protein, observed by retinal flat mount.

FIG. 10 illustrates degree of retinal degeneration in mice depending on the expression level of Nkx3.2 protein, observed through fundus image.

FIG. 11 illustrates degree of retinal degeneration in mice depending on the expression level of Nkx3.2 protein, observed through optical coherence tomography (OCT).

FIG. 12 illustrates degree of retinal degeneration in mice depending on the expression level of Nkx3.2 protein, observed through histopathology analysis.

FIG. 13 illustrates visual function preservation effects in mice depending on the expression level of Nkx3.2 protein, observed through electroretinography (ERG).

FIG. 14 illustrates cell viability, depending on $H_2O_2$ concentrations that induce oxidative stress, in human retinal pigment epithelial cells.

FIG. 15 illustrates cell death rate, depending on $H_2O_2$ concentrations that induce oxidative stress, in human retinal pigment epithelial cells.

FIG. 16 illustrates the expression level of Nkx3.2 protein and the expression level of cleaved PARP protein, a marker of cell death, depending on $H_2O_2$ concentrations that induce oxidative stress, in human retinal pigment epithelial cells, and they were detected through Western blot analysis.

FIG. 17 illustrates degree of cell death caused by oxidative stress, upon treatment with an Nkx3.2-expressing virus (Lenti-Nkx3.2), in human retinal pigment epithelial cells.

FIG. 18 illustrates degree of cell death caused by oxidative stress, upon treatment with a virus (sh-Nkx3.2) that inhibits Nkx3.2 expression, in human retinal pigment epithelial cells.

FIG. 19 illustrates ability of full-length Nkx3.2 and fragments thereof to inhibit retinal pigment epithelial cell death caused by oxidative stress, observed using a microplate reader device.

FIG. 20a illustrates transfection efficiency for full-length Nkx3.2 and fragments thereof, observed using an immunochemical technique.

FIGS. 20b and 20c illustrate results obtained by calculating the number of transfected Nkx3.2 proteins/number of DAPI-stained nuclei to obtain average values, and then representing the average values by a table (FIG. 20b) and a graph (FIG. 20c).

FIG. 21a illustrates images obtained by causing Nkx3.2-overexpressing mice to be irradiated with a laser so that choroidal neovascularization is induced, and then photographing retinal blood vessels by fundus angiography.

FIG. 21b illustrates a result obtained by comparing the difference in size of choroidal neovascular lesions between wild-type mice and Nkx3.2-overexpressing mice, based on the images photographed by fundus angiography.

FIG. 22a illustrates images obtained by causing Nkx3.2-overexpressing mice to be irradiated with a laser so that choroidal neovascularization is induced, and then photographing a retinal region by optical coherence tomography.

FIG. 22b illustrates a result obtained by comparing the difference in retinal edema between wild-type mice and Nkx3.2-overexpressing mice, based on the images photographed by optical coherence tomography.

BEST MODE FOR CARRYING OUT THE INVENTION

Hereinafter, the present invention will be described in detail.

In an aspect of the present invention, a pharmaceutical composition for preventing or treating retinal dystrophies, comprising, as an active ingredient, Nkx3.2 or a fragment thereof, is provided.

The term "Nkx3.2", as used herein, is also called NK3 homeobox 2 and is one of the proteins belonging to the NK-2 homeobox family. Nkx3.2 plays an important role in skeletal development and organ differentiation. In particular, Nkx3.2 is known to promote chondrogenic differentiation, delay chondrocyte hypertrophy, and inhibit chondrocyte cell death. The Nkx3.2 may be a human-derived protein. Here, the Nkx3.2 protein may have the amino acid sequence of SEQ ID NO: 7, which may be encoded by the nucleotide sequence of SEQ ID NO: 8.

The Nkx3.2 protein, as used herein, may include an amino acid sequence exhibiting substantial identity to the amino acid sequence of SEQ ID NO: 7. The Nkx3.2 protein having the above-mentioned substantial identity means an amino acid sequence exhibiting 80%, 90%, 95%, 98%, or 99% homology.

In addition, for the Nkx3.2 protein used in the present invention, a protein having its wild-type amino acid sequence as well as amino acid sequence variants thereof may be included within the scope of the present invention. Here, the variant of the Nkx3.2 protein refers to a protein having a sequence that varies from the wild-type amino acid sequence of the Nkx3.2 protein by deletion, insertion, non-conservative or conservative substitution, or a combination thereof of one or more amino acid residues. Amino acid exchanges in proteins and peptides, which do not totally alter molecular activity, are known in the art (H. Neurath, R. L. Hill, The Proteins, Academic Press, New York, 1979). The most commonly occurring exchanges are exchanges between amino acid residues Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly. In addition, the Nkx3.2 protein may be modified by phosphorylation, sulfation, acrylation, glycosylation, methylation, farnesylation, or the like.

The Nkx3.2 protein or a variant thereof may be extracted from natural sources or may be prepared by synthesis (Merrifield, J. Amer. Chem. Soc. 85:2149-2156, 1963) or by a DNA sequence-based recombinant method (Sambrook, J. et al., 2001. *Molecular Cloning. A Laboratory Manual*, $3^{rd}$ ed. Cold Spring Harbor Press).

The term "Nkx3.2 fragment", as used herein, may be a polypeptide represented by Formula (I):

N-terminal extension domain-core domain-C-terminal extension domain (I).

In Formula (I), the core domain is a polypeptide having the amino acid sequence of SEQ ID NO: 1. In addition, the N-terminal extension domain is a polypeptide having the amino acid sequence of SEQ ID NO: 3, in which 1 to 42 amino acids may be consecutively deleted from the N-terminus to the C-terminus direction, starting from the amino acid at position 1 of SEQ ID NO: 3. In addition, the C-terminal extension domain is a polypeptide having the amino acid sequence of SEQ ID NO: 5, in which 1 to 23 amino acids may be consecutively deleted from the C-terminus to the N-terminus direction, starting from the amino acid at position 24 of SEQ ID NO: 5.

The term "core domain", as used herein, refers to a polypeptide having an amino acid sequence from positions 166 to 309 of the full-length Nkx3.2 protein. The full-length Nkx3.2 protein may have the amino acid sequence of SEQ ID NO: 7. The core domain may have the amino acid sequence of SEQ ID NO: 1, which may be encoded by the nucleotide sequence of SEQ ID NO: 2.

The term "N-terminal extension domain", as used herein, refers to a domain that is bound to the N-terminus of the above-described core domain, the domain being a polypeptide having an amino acid sequence from positions 123 to 165 of the full-length Nkx3.2 protein. The N-terminal extension domain may have the amino acid sequence of SEQ ID NO: 3, which may be encoded by the nucleotide sequence of SEQ ID NO: 4.

The N-terminal extension domain may be a polypeptide having the amino acid sequence of SEQ ID NO: 3, or the same polypeptide in which 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, or 42 amino acid residues are deleted from the N-terminus to the C-terminus direction, starting from the amino acid at position 1 of the polypeptide.

The term "C-terminal extension domain", as used herein, refers to a domain that is bound to the C-terminus of the above-described core domain, the domain being a polypeptide having an amino acid sequence from positions 310 to 333 of the full-length Nkx3.2 protein. The C-terminal extension domain may have the amino acid sequence of SEQ ID NO: 5, which may be encoded by the nucleotide sequence of SEQ ID NO: 6.

The C-terminal extension domain is a polypeptide having an amino acid sequence of SEQ ID NO: 5, or the same polypeptide in which 1, 2, 3, 4, 5, 6, 7, 8, 9, 10, 11, 12, 13, 14, 15, 16, 17, 18, 19, 20, 21, 22, or 23 amino acid residues are deleted from the C-terminus to the N-terminus direction, starting from the amino acid at position 24 of the polypeptide.

Deletion of the amino acid residue(s) may occur in either or both domains of the N-terminal extension domain and the C-terminal extension domain. Specifically, the polypeptide in the present invention may have the amino acid sequence of SEQ ID NO: 1, 3, 5, 9, 10, 11, 12, 13, 14, 15, 16, 17, 18, 19, 20, 21, 22, 23, 24, 25, 26, 27, or 28.

The polypeptide is a fragment of the Nkx3.2 protein and does not exist in vivo. However, the polypeptide is not easily degraded in vivo while having the same activity as the wild-type Nkx3.2 protein. Thus, the polypeptide exists for a longer time in the body than the wild-type Nkx3.2 protein, thereby exhibiting superior activity.

In an embodiment, the present invention provides a polypeptide having the amino acid sequence of SEQ ID NO: 20 or a fragment thereof. The fragment may be a polypeptide having the amino acid sequence of SEQ ID NO: 20, in which 1 to 87 amino acids are consecutively deleted from the N-terminus to the C-terminus direction, starting from the amino acid at position 1 of SEQ ID NO: 20. In addition, the fragment may be a polypeptide having the amino acid sequence of SEQ ID NO: 20, in which 1 to 39 amino acids are consecutively deleted from the C-terminal to the N-terminal direction, starting from the amino acid at position 209 of SEQ ID NO: 20.

Deletion of the amino acid(s) may occur at either or both of the N-terminus and the C-terminus of the amino acid sequence of SEQ ID NO: 20.

In an embodiment of the present invention, to evaluate the ability of the full-length Nkx3.2 and fragments thereof to inhibit retinal pigment epithelial cell death caused by oxidative stress, a DNA plasmid for each of the full-length Nkx3.2 and fragments thereof was transfected into a retinal pigment epithelial cell line, and oxidative stress was induced therein. As a result, it was identified that all of the full-length Nkx3.2 and fragments thereof inhibited retinal pigment epithelial cell death.

In another aspect of the present invention, there is provided a pharmaceutical composition for preventing or treating retinal dystrophies, comprising, as an active ingredient, a polynucleotide encoding Nkx3.2 or a fragment thereof.

The polynucleotide may be DNA or RNA, in which the RNA may be mRNA. In addition, the polynucleotide may be loaded into a non-viral vector. The non-viral vector may be any one selected from the group consisting of plasmids, liposomes, cationic polymers, micelles, emulsions, solid lipid nanoparticles, and combinations thereof.

In addition, in yet another aspect of the present invention, there is provided a pharmaceutical composition for preventing or treating retinal dystrophies, comprising, as an active ingredient, a recombinant virus that contains a polynucleotide encoding Nkx3.2 or a fragment thereof.

The Nkx3.2 fragment may be a polypeptide represented by Formula (I):

N-terminal extension domain-core domain-C-terminal extension domain (I).

In Formula (I), the core domain is a polypeptide having the amino acid sequence of SEQ ID NO: 1. In addition, the N-terminal extension domain is a polypeptide having the amino acid sequence of SEQ ID NO: 3, in which 1 to 42 amino acids are consecutively deleted from the N-terminus to the C-terminus direction, starting from the amino acid at position 1 of SEQ ID NO: 3. In addition, the C-terminal extension domain is a polypeptide having the amino acid sequence of SEQ ID NO: 5, in which 1 to 23 amino acids are consecutively deleted from the C-terminus to the N-terminus direction, starting from the amino acid at position 24 of SEQ ID NO: 5. Here, the core domain, the N-terminal extension domain, and the C-terminal extension domain are as described above, and the polynucleotide may be a nucleotide sequence encoding the amino acid sequence of SEQ ID NO: 1, 3, 5, 9, 10, 11, 12, 13, 14, 15, 16, 17, 18, 19, 20, 21, 22, 23, 24, 25, 26, 27, or 28.

The virus may be any one selected from the group consisting of adenovirus, adeno-associated virus (AAV), retrovirus, lentivirus, herpes simplex virus, and vaccinia virus. Specifically, the virus may be adeno-associated virus (AAV). The adeno-associated virus is not limited to a specific serotype, and may preferably be any one of AAV1 to AAV9.

The adeno-associated virus (AAV) is suitable as a gene delivery system of the present invention because it is capable of infecting non-dividing cells and has an ability to infect various types of cells. Details on construction and use of AAV vectors are specifically disclosed in U.S. Pat. Nos. 5,139,941 and 4,797,368.

Typically, the AAV virus may be produced by co-transfection of a plasmid comprising a gene sequence of interest flanked by two AAV terminal repeats and an expression plasmid comprising a wild-type AAV coding sequence without terminal repeats.

The term "retinal dystrophy", as used herein, refers to a disease caused by damage that has occurred to the retina for reasons such as aging and disease. The retinal dystrophy may be any one selected from the group consisting of macular degeneration, diabetic retinopathy, choroidal neovascularization, and retinal edema.

The macular degeneration is a disease in which the macular function decreases as aging progresses, so that vision decreases or is lost. In a case where vision starts to decrease due to this disease, recovery to the original vision cannot be achieved. The disease is called age-related macular degeneration and is a leading cause of vision loss in old age. The macular degeneration is divided into two types: dry macular degeneration and wet macular degeneration. About 90% of patients suffering from macular degeneration have dry macular degeneration, and this dry macular degeneration occurs in a case where age-related deposits accumulate under the retina or lesions such as retinal pigment epithelial atrophy develop. As visual cells in the macula are slowly destroyed, the macular function decreases, and the central vision decreases over time. For wet macular degeneration, symptoms occur due to formation of abnormally many new blood vessels in the choroid that make up the lower layer of the macula. Wet macular degeneration progresses faster than dry macular degeneration, which may lead to a sharp drop in vision and lead to blindness within 2 months to 3 years.

Diabetic retinopathy is a complication that occurs in the retina of the eye due to peripheral circulatory disorder caused by diabetes. The disease may initially have no symptoms and may exhibit symptoms of decreased vision as its invasion into the macula occurs. Diabetic retinopathy may be divided into simple retinopathy, pre-proliferative retinopathy, and proliferative retinopathy, depending on the progression stage.

Choroidal neovascularization is a disease in which the choroid is damaged due to formation of abnormal blood vessels, so that visual impairment occurs. The choroidal neovascularization is one of the leading causes of irreversible vision loss worldwide. For the choroidal neovascularization, despite various therapeutic attempts, prognosis of vision is poor for most patients.

Retinal edema means that the retina is swollen. As a degeneration or abnormality occurs in fine blood vessels such as capillaries in the retina or macula for various reasons, bleeding may occur, resulting in retinal edema. In a case where edema occurs in the retina, various symptoms may occur, including decreased vision.

In the pharmaceutical composition comprising Nkx3.2 or a fragment thereof, a polypeptide, which is Nkx3.2 or a fragment thereof according to the present invention, may be contained in an amount of 10% to 95% by weight with respect to the total weight of the pharmaceutical composition. Also, in addition to the active ingredient, the pharmaceutical composition of the present invention may further comprise one or more active ingredients that exhibit the same or similar function. In addition to the above-described active ingredients, the pharmaceutical composition according to the present invention may further comprise one or more pharmaceutically acceptable carriers for administration.

In addition, a dose of the pharmaceutical composition, comprising, as an active ingredient, a recombinant virus that contains a polynucleotide encoding Nkx3.2 or a fragment thereof, may vary depending on various factors including type of disease, severity of disease, types and amounts of active ingredients and other ingredients contained in the pharmaceutical composition, type of formulation and the patient's age, weight, general health status, gender and diet, time of administration, route of administration, duration of treatment, and simultaneously used drugs.

The recombinant virus contained in the pharmaceutical composition according to the present invention may be administered in an amount of $1.0 \times 10^5$ to $1.0 \times 10^{15}$ viral genomes per day on an adult basis so that the pharmaceutical composition exhibits a desirable effect. Specifically, in a dose of the pharmaceutical composition of the present invention, the virus may be administered in an amount of $1.0 \times 10^5$ to $1.0 \times 10^{15}$, $1.0 \times 10^7$ to $1.0 \times 10^{13}$, $1.0 \times 10^8$ to $1.0 \times 10^{12}$, or $1.0 \times 10^9$ to $1.0 \times 10^{10}$ per day on an adult basis.

In addition, the present invention provides a method for preventing or treating retinal dystrophies, comprising a step of administering, to an individual, a pharmaceutical composition that comprises, as an active ingredient, Nkx3.2 or a fragment thereof; or a recombinant virus that contains a polynucleotide encoding Nkx3.2 or a fragment thereof.

A dose of the polypeptide that is Nkx3.2 or a fragment thereof; or the recombinant virus that contains a polynucleotide encoding Nkx3.2 or a fragment thereof, according to the present invention, may vary depending on various factors including type of disease, severity of disease, types and amounts of active ingredients and other ingredients contained in the pharmaceutical composition, type of formulation and the patient's age, weight, general health status, gender and diet, time of administration, route of administration, duration of treatment, and simultaneously used drugs.

In the pharmaceutical composition for preventing or treating retinal dystrophies, comprising, as an active ingredient, Nkx3.2 or a fragment thereof, according to the present invention, the polypeptide that is Nkx3.2 or a fragment thereof may be contained in an effective amount of 0.0001 to 100 mg/kg so that the pharmaceutical composition exhibits a desirable effect. Here, the administration may be performed once or several times a day.

In addition, in the pharmaceutical composition for preventing or treating retinal dystrophies, comprising, as an active ingredient, a recombinant virus that contains a polynucleotide encoding Nkx3.2 or a fragment thereof, according to the present invention, the recombinant virus may be administered in an amount of $1.0 \times 10^5$ to $1.0 \times 10^{15}$ viral genomes per day on an adult basis so that the pharmaceutical composition exhibits a desirable effect. Specifically, in the pharmaceutical composition of the present invention, the virus may be administered in an amount of $1.0 \times 10^5$ to $1.0 \times 10^{15}$, $1.0 \times 10^7$ to $1.0 \times 10^{13}$, $1.0 \times 10^8$ to $1.0 \times 10^{12}$, or $1.0 \times 10^9$ to $1.0 \times 10^{10}$ per day on an adult basis.

In addition, the pharmaceutical composition of the present invention may be administered to an individual in need thereof by various methods known in the art. The individual may be a mammal, specifically a human. The route of administration may be appropriately selected by a person skilled in the art in consideration of administration method, body fluid volume, viscosity, and the like. Specifically, the administration may be performed via any one selected from the group consisting of intravenous, intraarterial, intraperitoneal, intramuscular, intrasternal, transdermal, intranasal, inhalation, topical, rectal, oral, intraocular, and intradermal routes.

In yet another aspect of the present invention, there is provided a method for preparing an Nkx3.2 fragment with increased in vivo stability, comprising a step of deleting, from a polypeptide having the amino acid sequence of SEQ ID NO: 7, any one region selected from the group consisting of the N-terminal region, the C-terminal region, and a combination thereof.

Deletion of the N-terminal region may be made such that 1 to 199 amino acids are consecutively deleted from the N-terminus to the C-terminal direction, starting from the amino acid at position 1 of SEQ ID NO: 7. In an embodiment, deletion of the N-terminal region may be made such that 41, 98, 111, or 122 amino acids are consecutively deleted from the N-terminus to the C-terminal direction, starting from the amino acid at position 1 of SEQ ID NO: 7. The Nkx3.2 fragment, obtained by deleting the N-terminal region from the polypeptide having the amino acid sequence of SEQ ID NO: 7, may have the amino acid sequence of SEQ ID NO: 11, SEQ ID NO: 12, SEQ ID NO: 13, or SEQ ID NO: 14. Specifically, the deletion may be made such that 1 to 99 amino acids are consecutively deleted from the N-terminus to the C-terminus direction, starting from the amino acid at position 100 of SEQ ID NO: 7.

Deletion of the C-terminal region may be made such that 1 to 52 amino acids are consecutively deleted from the C-terminus to the N-terminal direction, starting from the amino acid at position 333 of SEQ ID NO: 7. In an embodiment, deletion of the C-terminal region may be made such that 13 or 26 amino acids are consecutively deleted from the C-terminal to the N-terminal direction, starting from the amino acid at position 333 of SEQ ID NO: 7. The Nkx3.2 fragment, obtained by deleting the C-terminal region from the polypeptide having the amino acid sequence of SEQ ID NO: 7, may have the amino acid sequence of SEQ ID NO: 9 or 10. Specifically, the deletion may be made such that 1 to 39 amino acids are consecutively deleted from the C-terminus to the N-terminus direction, starting from the amino acid at position 320 of SEQ ID NO: 7.

Deletion of the amino acids may occur at either or both of the N-terminal region and the C-terminal region. In an embodiment, deletion of the amino acids may be made such that 98 to 164 amino acids, specifically 98, 104, 109, 111, 122, 129, 149, 152, 155, 158, 161, or 164 amino acids are consecutively deleted from the N-terminal direction to the C-terminal direction, starting from the amino acid at position 1 of SEQ ID NO: 7, and at the same time, 3 to 23 amino acids, specifically, 3, 6, 9, 13, 15, 17, 19, 21, or 23 amino acids are consecutively deleted from the C-terminal direction to the N-terminal direction, starting from the amino acid at position 333 of SEQ ID NO: 7.

The Nkx3.2 fragment, obtained by deleting amino acids in both the N-terminal region and the C-terminal region, may have any one amino acid sequence of SEQ ID NOs: 15 to 28. Deletion of the amino acid residues in both the N-terminal region and the C-terminal region can be carried out by a person skilled in the art using appropriate methods.

Embodiment of the Invention

Hereinafter, the present invention will be described in detail by way of the following examples. However, the following examples are only to illustrate the present invention, and the present invention is not limited thereto.

Preparation Example 1. Preparation of Experimental Ocular Tissue

C57BL/6 mice were purchased and kept under a specific sterile condition in an approved animal facility. According to a predetermined experimental protocol, the eyes of normal C57BL/6 mice were excised and the tissue was separated therefrom.

In addition, human ocular tissue was purchased and kept under a specific sterile condition in an approved facility.

Experimental Example 1. Identification of Expression of Nkx3.2 in Retinal Pigment Epithelial Cells Since expression of the Nkx3.2 protein in the ocular retinal pigment epithelium had never been reported, verification therefor was made using immunohistochemistry (IHC) staining and Western blot analysis.

In the C57BL/6 mouse ocular tissue and the human ocular tissue prepared in Preparation Example 1, expression of the Nkx3.2 protein was identified using immunohistochemistry staining. The results are illustrated in FIGS. 1 and 2.

In addition, the cornea and the retinal pigment epithelium (RPE) were separated from the human ocular tissue prepared in Preparation Example 1, and the proteins were extracted therefrom. Expression of the Nkx3.2 protein was identified through Western blot analysis. The results are illustrated in FIG. 3.

As illustrated in FIGS. 1 and 2, expression of the Nkx3.2 protein was identified in the C57BL/6 mouse and human ocular tissues along with RPE65 protein that was specifically expressed in retinal pigment epithelial cells. In addition, as illustrated in FIG. 3, it was identified that the Nkx3.2 protein was expressed higher in the hind (H) part of the eye where RPE65 was highly expressed than in the frontal (F) part of the eye.

Experimental Example 2. Identification of Expression of Nkx3.2 in Retinal Degeneration Model Induced by Oxidative Stress Immunohistochemistry (IHC) staining and Western blot analysis were used to identify expression of Nkx3.2 protein in a retinal degeneration model induced by oxidative stress.

The retinal degeneration mouse model was constructed by inducing oxidative stress, in the eyes of the C57BL/6 mice prepared in Preparation Example 1, using sodium iodate ($NaIO_3$). Then, lesions in the retinal degeneration mouse model were observed using a microscope. In addition, expression of the Nkx3.2 protein in the retinal degeneration mouse model was identified using immunohistochemistry staining. The results are illustrated in FIGS. 4 and 5.

In addition, proteins were extracted from the tissue of the retinal degeneration mouse model and subjected to Western blot analysis, to identify expression of the Nkx3.2 protein. The results are illustrated in FIG. 6.

As illustrated in FIG. 4, the retinal pigment epithelial lesion was identified in the retinal degeneration mouse model constructed by inducing oxidative stress using NaIO$_3$. In addition, as illustrated in FIG. 5, it was identified that the Nkx3.2 protein was decreased in the retinal degeneration mouse model in which the retinal pigment epithelial lesion was identified.

In addition, as illustrated in FIG. 6, it was identified that expression of the Nkx3.2 protein was remarkably decreased in the retinal degeneration model induced by oxidative stress, and such a decrease was an initial change preceding a decrease in RPE65 which is a marker of the retinal pigment epithelium.

Experimental Example 3. Generation of Mice Overexpressing Nkx3.2 in Retinal Pigment Epithelial Cells In a previous paper, the present research team reported Cre-dependent Nkx3.2-overexpressing mice (Jeong, Da-Un, Je-Yong Choi, and Dae-Won Kim. "Cartilage-Specific and Cre-Dependent Nkx3.2 Overexpression In Vivo Causes Skeletal Dwarfism by Delaying Cartilage Hypertrophy." *Journal of cellular physiology* 232.1 (2017): 78-90). Based on this, BEST1-Cre mice, in which Cre is expressed specifically in retinal pigment epithelial cells, were engineered such that overexpression of Nkx3.2 by Cre gene recombinase occurs only in retinal pigment epithelial cells. Production strategy for the corresponding mice is schematically illustrated in FIG. 7.

In addition, expression of Nkx3.2 in the retinal pigment epithelial cells of the produced Nkx3.2-overexpressing mice was identified through immunohistochemistry staining, and the results are illustrated in FIG. 8.

As illustrated in FIG. 8, for the mice produced such that overexpression of Nkx3.2 by Cre gene recombinase occurs only in retinal pigment epithelial cells, overexpression of the Nkx3.2 protein was verified in the retinal pigment epithelial cells.

Experimental Example 4. Identification of Retinal Pigment Epithelial Cell Inhibition Effect Caused by Overexpression of Nkx3.2

For the mice produced in Experimental Example 3 in which Nkx3.2 was overexpressed specifically in retinal pigment epithelial cells, retinal degeneration was induced by oxidative stress generated using NaIO$_3$.

Experimental Example 4.1. Retinal Flat Mount

For the mice in which retinal degeneration was induced by oxidative stress, the hemispherical retina was flat-mounted to identify retinal degenerative lesions. The results are illustrated in FIG. 9.

As illustrated in FIG. 9, in the Nkx3.2 protein-non-overexpressing (ci-Nkx3.2) mice, retinal degeneration caused by oxidative stress was clearly observed. On the other hand, in the Nkx3.2-overexpressing (ciTg-Nkx3.2) mice, retinal degeneration caused by oxidative stress was not observed.

Experimental Example 4.2. Fundus Image

The ocular retinal structure of the mice, in which retinal degeneration was induced by oxidative stress, was analyzed by fundus image. The results are illustrated in FIG. 10.

As illustrated in FIG. 10, the normal control group (Norm) exhibited a uniform and even form of retinal curve around the optic nerve and exhibited normal retinal reflection. On the other hand, the retinal degeneration group of Nkx3.2-non-overexpressing mice (AMD) exhibited split retinal pigment epithelium and exhibited low reflection pattern. In contrast, the retinal degeneration group of Nkx3.2-overexpressing mice (AMD+Nkx3.2) exhibited a similar retinal structure to that of the normal control group.

Experimental Example 4.3. Optical Coherence Tomography

The ocular retinal structure of mice, in which retinal degeneration was induced by oxidative stress, was analyzed using optical coherence tomography. The results are illustrated in FIG. 11.

As illustrated in FIG. 11, the normal control group (Norm) well exhibited a multilayered structure of the retina, whereas the retinal degeneration group of Nkx3.2-non-overexpressing mice (AMD) had severe retinal degeneration and exhibited a severely damaged multilayered structure of the retina. In contrast, the retinal degeneration group of Nkx3.2-overexpressing mice (AMD+Nkx3.2) exhibited a similar retinal structure to that of the normal control group.

Experimental Example 4.4. Histopathological Analysis

The ocular retinal structure of the mice, in which retinal degeneration was induced by oxidative stress, was histologically analyzed. The results are illustrated in FIG. 12.

As illustrated in FIG. 12, the normal control group (Norm) exhibited a normal structure in the retina and a normal membrane structure in the retinal pigment epithelium. On the other hand, the retinal degeneration group of Nkx3.2-non-overexpressing mice (AMD) exhibited the retinal pigment epithelium that was severely damaged and lost. In contrast, the retinal degeneration group of Nkx3.2-overexpressing mice (AMD+Nkx3.2) exhibited similar retinal structure and retinal pigment epithelial pattern to those of the normal control group.

Experimental Example 5. Identification of Visual Function Preservation Effect Caused by Overexpression of Nkx3.2

A visual function preservation effect caused by overexpression of Nkx3.2 was identified through electroretinography (ERG).

For the mice in which retinal degeneration was induced by oxidative stress in Experimental Example 4 and in which Nkx3.2 was overexpressed specifically in retinal pigment epithelial cells, their visual function was analyzed through ERG. The results are illustrated in FIG. 13.

As illustrated in FIG. 13, the normal control group (Normal) exhibited a normal retinal potential change in response to an external light stimulus applied to the retina. On the other hand, the retinal degeneration group of Nkx3.2-non-overexpressing mice (AMD) had complete disappearance of a retinal potential change occurring in response to an external light stimulus. In contrast, the retinal degeneration group of Nkx3.2-overexpressing mice (AMD+Nkx3.2) exhibited a similar retinal potential change to that of the normal control group.

Experimental Example 6. Identification of Cell Viability, Cell Death Rate, and Expression of Nkx3.2 Protein, Depending on $H_2O_2$ Concentrations that Induce Oxidative Stress Human retinal pigment epithelial cells were treated with 400 μM, 600 μM, 800 μM, and 1 mM hydrogen peroxide ($H_2O_2$), respectively, to induce oxidative stress. Thereafter, cell viability, depending on $H_2O_2$ concentrations that induce oxidative stress, was measured using a water-soluble tetrazolium salt assay (WST). The results are illustrated in FIG. 14.

In addition, a cell death rate in the human retinal pigment epithelial cells, in which oxidative stress was induced by treatment with the above-mentioned respective $H_2O_2$ concentrations, was measured using an annexin V-FITC apoptosis kit (Sigma-Aldrich). In addition, changes in expression level of the Nkx3.2 protein, depending on increased cell death rate, were measured through Western blot analysis. The results are illustrated in FIGS. 15 and 16.

As illustrated in FIG. 14, the cell viability decreased as the $H_2O_2$ concentration increased. In addition, as illustrated in FIG. 15, the cell death rate increased as the $H_2O_2$ concentration increased. As illustrated in FIG. 16, expression of cleaved PARP protein, which is an apoptotic marker, increased as the $H_2O_2$ concentration increased. That is, it was verified at the protein level that increased expression of the cleaved PARP protein, which is an apoptotic marker, caused cell death. In addition, it was identified that expression of the Nkx3.2 protein decreased as expression of the cleaved PARP protein increased.

Experimental Example 7. Measurement of Cell Death Rate after Administration of Nkx3.2 Protein-Expressing Virus Human retinal pigment epithelial cells were treated with 800 μM $H_2O_2$, to induce oxidative stress. The oxidative stress-induced cells were divided into two groups. One group was administered the Nkx3.2-expressing virus (Lenti-Nkx3.2), and the other group was administered the virus (sh-Nkx3.2) with suppressed expression of Nkx3.2. Thereafter, a cell death rate caused by oxidative stress in the human retinal pigment epithelial cells, depending on the administration of each virus, was measured using the annexin V-FITC apoptosis kit. The results are illustrated in FIGS. 17 and 18.

As illustrated in FIG. 17, in a case where the human retinal pigment epithelial cells were administered the Nkx3.2-expressing virus (Lenti-Nkx3.2), the cell death rate caused by $H_2O_2$ was decreased as compared with the control virus (Lenti-Ctrl)-administered group. In addition, as illustrated in FIG. 18, in a case where the human retinal pigment epithelial cells were administered the virus (sh-Nkx3.2) with suppressed expression of Nkx3.2, the cell death rate caused by $H_2O_2$ was increased as compared with the control virus (sh-Ctrl)-administered group.

Experimental Example 8. Evaluation of Ability of Nkx3.2 Protein and Fragments Thereof to Inhibit Retinal Pigment Epithelial Cell Death Caused by Oxidative Stress

Experimental Example 8.1. Evaluation of Ability of Full-Length Nkx3.2 Protein and Fragments Thereof to Inhibit Retinal Pigment Epithelial Cell Death Caused by Oxidative Stress To evaluate whether the full-length Nkx3.2 and fragments thereof have a function of inhibiting retinal pigment epithelial cell death caused by $H_2O_2$, which is an oxidative stress, ARPE19 cells were seeded in a 12-well plate (3E+4 cells/well) and transfection was carried out with 0.6 μg of a DNA plasmid encoding each of the following: the full-length hNkx3.2 (SEQ ID NO: 7), and fragments of hNkx3.2 which have, respectively, the amino acid sequence of SEQ ID NO: 9 (amino acid residues 1-320 of the full-length hNkx3.2 sequence), SEQ ID NO: 10 (amino acid residues 1-307 of the full-length hNkx3.2 sequence), SEQ ID NO: 12 (amino acid residues 99-333 of the full-length hNkx3.2 sequence), SEQ ID NO: 13 (amino acid residues 112-333 of the full-length hNkx3.2 sequence), SEQ ID NO: 20 (amino acid residues 112-320 of the full-length hNkx3.2 sequence), SEQ ID NO: 21 (amino acid residues 123-320 of the full-length hNkx3.2 sequence), SEQ ID NO: 23 (amino acid residues 150-320 of the full-length hNkx3.2 sequence), and SEQ ID NO: 28 (amino acid residues 165-310 of the full-length hNkx3.2 sequence).

36 hours after transfection, reaction with 0.3 mM $H_2O_2$ was allowed to proceed in a $CO_2$ incubator at 37° C. for 15 hours. 50 μl of water-soluble tetrazolium salt was added to each well, and then reaction was allowed to proceed in a $CO_2$ incubator at 37° C. for 90 minutes. 150 ul of the supernatant was taken from each well and transferred to a 96-well plate. Absorbance was measured at a wavelength of 450 nm using a microplate reader device. The results are illustrated in FIG. 19.

As illustrated in FIG. 19, the Nkx3.2 fragments, including the full-length Nkx3.2, inhibited ARPE19 cell death caused by $H_2O_2$ from as little as 8% to as much as 17% as compared with the control group.

Experimental Example 8.2. Evaluation of Transfection Efficiency for Full-Length Nkx3.2 and Fragments Thereof Due to the fact that 100% efficiency does not appear given the characteristics of transfection, there is a possibility that in the cell viability analysis performed in the above experimental example, the ability of the full length Nkx3.2 and fragments thereof to inhibit retinal pigment epithelial cell death caused by $H_2O_2$ was undervalued. In this regard, the transfection efficiency for the full-length Nkx3.2 and fragments thereof was evaluated using an immunocytochemistry technique. First, AREP19 cells were seeded in a 12-well plate containing a slide glass with 2E+4 cells/well. Transfection was performed with 0.6 μg of DNA plasmid encoding each of the full-length hNkx3.2 or fragments thereof. After 48 hours, 2% paraformaldehyde was added to each well and reaction was allowed to proceed at room temperature for 15 minutes, so that the cells were fixed. Thereafter, 0.1% TRITON® X-100 solution in 0.1% sodium citrate was added to each well and reaction was allowed to proceed at room temperature for 30 minutes, so that the cells were made in a state where antibodies easily penetrate the cells. Then, washing with PBS was performed twice.

0.1% TRITON® X-100 solution in 5% goat serum was added to each well and reaction was allowed to proceed at room temperature for 30 minutes, so that non-specific staining of antibodies was decreased. Then, washing with 0.05% Tween 20 in PBS (PBST) was performed twice. The primary antibody (Nkx3.2-rabbit) was diluted in a ratio of 1:500 and added thereto. Reaction was allowed to proceed 4° C. for 16 hours and washing with PBST was performed 5 times. The secondary antibody (FITC-anti-rabbit) was diluted in a ratio of 1:300 and added thereto. Reaction was allowed to proceed at room temperature for 30 minutes and washing with PBST was performed 5 times. DAPI was diluted in a ratio of 1:500 and added thereto. Reaction was allowed to proceed at room temperature for 10 minutes and washing with PBST was performed twice. The slide glass was wiped off with 70% EtOH. Then, mounting was performed with an anti-fading mounting solution and drying was performed in a dark room for 24 hours. Then, each sample was photographed with an upright microscope. Each sample was photographed in its column section. The number of transfected Nkx3.2 proteins per DAPI staining was counted and the average value was calculated. The results are illustrated in FIGS. 20a to 20c.

FIG. 20a illustrates the transfected Nkx3.2 and DAPI-stained nuclei, which were observed using an immunocytochemistry technique. As illustrated in FIGS. 20b and 20c, the transfection efficiency for the full-length Nkx3.2 and fragments thereof with respect to ARPE19 cells was between 15% and 31%.

Experimental Example 8.3. Re-Evaluation of Ability of Full-Length Nkx3.2 and Fragments Thereof to Inhibit Retinal Pigment Epithelial Cell Death Caused by Oxidative Stress, Depending on their Transfection Efficiency In consideration of the transfection efficiency for the full-length Nkx3.2 and fragments thereof, re-evaluation was performed on whether they could inhibit ARPE19 cell death caused by $H_2O_2$. The results are shown in Table 1 below.

contrast agent, and fundus fluorescence angiography (FAA) was performed on retinal blood vessels. Based on the images obtained from the fundus fluorescence angiography, CTF of the choroidal neovascular lesion was measured. A comparison was made, in terms of difference in size of the choroidal neovascular lesion, between the wild-type mice and the Nkx3.2-overexpressing mice. The results are illustrated in FIGS. 21a and 21b.

As illustrated in FIGS. 21a and 21b, a significantly decreased CTF value (29414.8±43200.47) for the choroidal neovascular lesion was observed in Nkx3.2-overexpressing mice (G2) as compared with that (124942.3±91743.74) in the wild-type mice (G1) ($P<0.05$). From these results, it was found that Nkx3.2 played an important role in inhibiting choroidal neovascularization.

Experimental Example 10. Identification of Retinal Edema Inhibition Effect Caused by Overexpression of Nkx3.2

The mice, in which Nkx3.2 was overexpressed specifically in retinal pigment epithelial cells, were irradiated with a laser to induce choroidal neovascularization. Then, on Day 9, optical coherence tomography was performed on the choroidal neovascularization-induced retinal region. Based on the images obtained from the optical coherence tomography, a comparison was made, in terms of difference in retinal edema pattern caused by the choroidal neovascular

TABLE 1

| Construct's SEQ ID NO | Measured cell viability enhancement (%) | Transfection efficiency for each construct (%) | Adjusted cell viability enhancement (%) |
|---|---|---|---|
| SEQ ID NO: 7 (Nkx3.2) | 11 | 25 | 44.0 |
| SEQ ID NO: 10 (amino acid residues 1-307 of full-length Nkx3.2 sequence) | 17 | 23 | 73.9 |
| SEQ ID NO: 12 (amino acid residues 99-333 of full-length Nkx3.2 sequence) | 13 | 31 | 41.9 |
| SEQ ID NO: 13 (amino acid residues 112-333 of full-length Nkx3.2 sequence) | 14 | 31 | 45.2 |
| SEQ ID NO: 20 (amino acid residues 112-320 of full-length Nkx3.2 sequence) | 9 | 26 | 34.6 |
| SEQ ID NO: 21 (amino acid residues 123-320 of full-length Nkx3.2 sequence) | 8 | 26 | 30.8 |
| SEQ ID NO: 23 (amino acid residues 150-320 of full-length Nkx3.2 sequence) | 12 | 16 | 75.0 |
| SEQ ID NO: 28 (amino acid residues 165-310 of full-length Nkx3.2 sequence) | 10 | 15 | 50.0 |

As shown in Table 1, the Nkx3.2 fragments as well as the full-length Nkx3.2, inhibited ARPE19 cell death caused by $H_2O_2$ from as little as 30% to as much as 75%, as compared with the control group.

Experimental Example 9. Identification of Choroidal Neovascularization Inhibition Effect Caused by Overexpression of Nkx3.2

The mice, in which Nkx3.2 was overexpressed specifically in retinal pigment epithelial cells, were irradiated with a laser to induce choroidal neovascularization (CNV). After 9 days, the mice were intraperitoneally injected with a lesion, between the wild-type mice and the Nkx3.2-overexpressing mice. The results are illustrated in FIGS. 22a and 22b.

As illustrated in FIGS. 22a and 22b, with respect to the choroidal neovascular lesion, a significantly decreased retinal thickness (220.6±10.47 microns) was observed in the Nkx3.2-overexpressing mice (G2) as compared with that (259.8±13.08 microns) in the wild-type mice (G1) ($P<0.01$). From these results, it was found that the retinal edema, which occurred secondarily due to the blood retinal barrier destroyed in the process of inducing choroidal neovascularization, was significantly decreased in the Nkx3.2-overexpressing mice as compared with the wild-type mice.

The invention claimed is:

1. A method for treating a retinal dystrophy in a subject in need thereof, comprising
administering to the subject a composition comprising, as an active ingredient,
(a) Nkx3.2 peptide of SEQ ID NO: 7, or
(b) a polynucleotide encoding Nkx3.2 peptide of SEQ ID NO: 7,
wherein the retinal dystrophy is selected from the group consisting of macular degeneration, diabetic retinopathy, choroidal neovascularization, and retinal edema.

2. The method of claim 1, wherein the administration is performed via any one selected from the group consisting of intravenous, intraarterial, intraperitoneal, intramuscular, intrasternal, transdermal, intranasal, inhalation, topical, rectal, oral, intraocular, and intradermal routes.

3. The method of claim 1, wherein the macular degeneration is dry macular degeneration or wet macular degeneration.

4. The method of claim 1, wherein the polynucleotide is included in a virus.

5. The method of claim 4, wherein the virus is any one selected from the group consisting of adenovirus, adeno-associated virus (AAV), retrovirus, lentivirus, herpes simplex virus, and vaccinia virus.

* * * * *

SEQUENCE LISTING

<160> NUMBER OF SEQ ID NOS: 28

<210> SEQ ID NO 1
<211> LENGTH: 144
<212> TYPE: PRT
<213> ORGANISM: Artificial Sequence
<220> FEATURE:
<223> OTHER INFORMATION: 166-309 aa fragment of Nkx3.2

<400> SEQUENCE: 1

```
Gly Val Gly Pro Arg Gly Ala His Val Ser Ala Leu Cys Ser Gly Ala
1               5                   10                  15

Gly Gly Gly Gly Ser Gly Pro Ala Gly Val Ala Glu Glu Glu Glu Glu
            20                  25                  30

Glu Pro Ala Ala Pro Lys Pro Arg Lys Lys Arg Ser Arg Ala Ala Phe
        35                  40                  45

Ser His Ala Gln Val Phe Glu Leu Glu Arg Arg Phe Asn His Gln Arg
    50                  55                  60

Tyr Leu Ser Gly Pro Glu Arg Ala Asp Leu Ala Ala Ser Leu Lys Leu
65                  70                  75                  80

Thr Glu Thr Gln Val Lys Ile Trp Phe Gln Asn Arg Arg Tyr Lys Thr
                85                  90                  95

Lys Arg Arg Gln Met Ala Ala Asp Leu Leu Ala Ser Ala Pro Ala Ala
            100                 105                 110

Lys Lys Val Ala Val Lys Val Leu Val Arg Asp Asp Gln Arg Gln Tyr
        115                 120                 125

Leu Pro Gly Glu Val Leu Arg Pro Pro Ser Leu Leu Pro Leu Gln Pro
    130                 135                 140
```

<210> SEQ ID NO 2
<211> LENGTH: 432
<212> TYPE: DNA
<213> ORGANISM: Artificial Sequence
<220> FEATURE:
<223> OTHER INFORMATION: nucleotide sequence encoding 166-309 aa
      fragment of Nkx3.2

<400> SEQUENCE: 2

```
ggtgttggcc ccagaggtgc acacgtgtcc gcgctgtgca gcggggccgg cggcggggc      60 ggcagcgggc cggcaggcgt cgcggaggag gaggaggagc cggcggcgcc caagccacgc    120
aagaagcgct cgcgggccgc tttctcccac gcgcaggtct tcgagctgga gcgccgcttt    180
aaccaccagc gctacctgtc cgggcccgag cgcgcagacc tggccgcgtc gctgaagctc    240
accgagacgc aggtgaaaat ctggttccag aaccgtcgct acaagacaaa gcgccggcag    300
atggcagccg acctgctggc ctcggcgccc gccgccaaga aggtggccgt aaaggtgctg    360
gtgcgcgacg accagagaca ataccctgccc ggcgaagtgc tgcggccacc ctcgcttctg    420
ccactgcagc cc                                                        432
```

<210> SEQ ID NO 3
<211> LENGTH: 43
<212> TYPE: PRT
<213> ORGANISM: Artificial Sequence
<220> FEATURE:
<223> OTHER INFORMATION: 123-165 aa fragment of Nkx3.2

<400> SEQUENCE: 3

```
Leu Ser Leu Gly Gln Pro Val Cys Glu Leu Ala Ala Ser Lys Asp Leu
1               5                   10                  15
```

```
Glu Glu Glu Ala Ala Gly Arg Ser Asp Ser Glu Met Ser Ala Ser Val
            20                  25                  30

Ser Gly Asp Arg Ser Pro Arg Thr Glu Asp Asp
        35                  40

<210> SEQ ID NO 4
<211> LENGTH: 129
<212> TYPE: DNA
<213> ORGANISM: Artificial Sequence
<220> FEATURE:
<223> OTHER INFORMATION: nucleotide sequence encoding 123-165 aa
      fragment of Nkx3.2

<400> SEQUENCE: 4
ttgagcctcg gccagccggt ctgtgagctg ccgcttcca aagacctaga ggaggaagcc     60
gcgggccgga gcgacagcga gatgtccgcc agcgtctcag gcgaccgcag cccaaggacc    120
gaggacgac                                                            129

<210> SEQ ID NO 5
<211> LENGTH: 24
<212> TYPE: PRT
<213> ORGANISM: Artificial Sequence
<220> FEATURE:
<223> OTHER INFORMATION: 310-333 aa fragment of Nkx3.2

<400> SEQUENCE: 5

Ser Tyr Tyr Tyr Pro Tyr Tyr Cys Leu Pro Gly Trp Ala Leu Ser Thr
1               5                   10                  15

Cys Ala Ala Ala Ala Gly Thr Gln
            20

<210> SEQ ID NO 6
<211> LENGTH: 72
<212> TYPE: DNA
<213> ORGANISM: Artificial Sequence
<220> FEATURE:
<223> OTHER INFORMATION: nucleotide sequence encoding 310-333 aa
      fragment of Nkx3.2

<400> SEQUENCE: 6
tcctactatt acccgtacta ctgcctccca ggctgggcgc tctccacctg cgcagctgcc     60
gcaggcaccc ag                                                        72

<210> SEQ ID NO 7
<211> LENGTH: 333
<212> TYPE: PRT
<213> ORGANISM: Homo Sapiens
<220> FEATURE:
<223> OTHER INFORMATION: Nkx3.2

<400> SEQUENCE: 7

Met Ala Val Arg Gly Ala Asn Thr Leu Thr Ser Phe Ser Ile Gln Ala
1               5                   10                  15

Ile Leu Asn Lys Lys Glu Glu Arg Gly Gly Leu Ala Ala Pro Glu Gly
            20                  25                  30

Arg Pro Ala Pro Gly Gly Thr Ala Ala Ser Val Ala Ala Ala Pro Ala
        35                  40                  45

Val Cys Cys Trp Arg Leu Phe Gly Glu Arg Asp Ala Gly Ala Leu Gly
    50                  55                  60

Gly Ala Glu Asp Ser Leu Leu Ala Ser Pro Ala Gly Thr Arg Thr Ala
65                  70                  75                  80
```

```
Ala Gly Arg Thr Ala Glu Ser Pro Glu Gly Trp Asp Ser Asp Ser Ala
                85                  90                  95

Leu Ser Glu Glu Asn Glu Ser Arg Arg Cys Ala Asp Ala Arg Gly
            100                 105                 110

Ala Ser Gly Ala Gly Leu Ala Gly Gly Ser Leu Ser Leu Gly Gln Pro
            115                 120                 125

Val Cys Glu Leu Ala Ala Ser Lys Asp Leu Glu Glu Glu Ala Ala Gly
130                 135                 140

Arg Ser Asp Ser Glu Met Ser Ala Ser Val Ser Gly Asp Arg Ser Pro
145                 150                 155                 160

Arg Thr Glu Asp Asp Gly Val Gly Pro Arg Gly Ala His Val Ser Ala
                165                 170                 175

Leu Cys Ser Gly Ala Gly Gly Gly Gly Ser Gly Pro Ala Gly Val
            180                 185                 190

Ala Glu Glu Glu Glu Pro Ala Ala Pro Lys Pro Arg Lys Lys Arg
            195                 200                 205

Ser Arg Ala Ala Phe Ser His Ala Gln Val Phe Glu Leu Glu Arg Arg
            210                 215                 220

Phe Asn His Gln Arg Tyr Leu Ser Gly Pro Glu Arg Ala Asp Leu Ala
225                 230                 235                 240

Ala Ser Leu Lys Leu Thr Glu Thr Gln Val Lys Ile Trp Phe Gln Asn
                245                 250                 255

Arg Arg Tyr Lys Thr Lys Arg Arg Gln Met Ala Ala Asp Leu Leu Ala
                260                 265                 270

Ser Ala Pro Ala Ala Lys Lys Val Ala Lys Val Leu Val Arg Asp
            275                 280                 285

Asp Gln Arg Gln Tyr Leu Pro Gly Glu Val Leu Arg Pro Pro Ser Leu
290                 295                 300

Leu Pro Leu Gln Pro Ser Tyr Tyr Tyr Pro Tyr Tyr Cys Leu Pro Gly
305                 310                 315                 320

Trp Ala Leu Ser Thr Cys Ala Ala Ala Gly Thr Gln
                325                 330
```

<210> SEQ ID NO 8
<211> LENGTH: 1002
<212> TYPE: DNA
<213> ORGANISM: Homo Sapiens
<220> FEATURE:
<223> OTHER INFORMATION: Nkx3.2

<400> SEQUENCE: 8

| | | | | | |
|---|---|---|---|---|---|
| atggctgtgc | gcggcgccaa | caccttgacg | tccttctcca | tccaggcgat | cctcaacaag | 60 |
| aaagaggagc | gcggcgggct | ggccgcgcca | gaggggcgcc | cggcgcccgg | gggcacagcg | 120 |
| gcatcggtgg | ccgcggctcc | cgctgtctgc | tgttggcggc | tctttgggga | gagggacgcg | 180 |
| ggcgcgttgg | ggggcgccga | ggactctctg | ctggcgtctc | ctgccggtac | cagaacagct | 240 |
| gcggggcgga | ctgcggagag | cccggaaggc | tgggactcgg | actccgcgct | cagcgaggag | 300 |
| aacgagagca | gcggcgcctg | cgcggacgcg | cgggggggcca | gcggggccgg | ccttgcgggg | 360 |
| ggatccttga | gcctcggcca | gccggtctgt | gagctggccg | cttccaaaga | cctagaggag | 420 |
| gaagccgcgg | gccggagcga | cagcgagatg | tccgccagcg | tctcaggcga | ccgcagccca | 480 |
| aggaccgagg | acgacggtgt | tggccccaga | ggtgcacacg | tgtccgcgct | gtgcagcggg | 540 |
| gccggcggcg | ggggcggcag | cgggccggca | ggcgtcgcgg | aggaggagga | ggagccggcg | 600 |
| gcgcccaagc | cacgcaagaa | gcgctcgcgg | gccgctttct | cccacgcgca | ggtcttcgag | 660 |

```
ctggagcgcc gctttaacca ccagcgctac ctgtccgggc ccgagcgcgc agacctggcc    720
gcgtcgctga agctcaccga gacgcaggtg aaaatctggt tccagaaccg tcgctacaag    780
acaaagcgcc ggcagatggc agccgacctg ctggcctcgg cgcccgccgc caagaaggtg    840
gccgtaaagg tgctggtgcg cgacgaccag agacaatacc tgcccggcga agtgctgcgg    900 ccacccctcgc ttctgccact gcagccctcc tactattacc cgtactactg cctcccaggc    960
tgggcgctct ccacctgcgc agctgccgca ggcacccagt ga                      1002
```

<210> SEQ ID NO 9
<211> LENGTH: 320
<212> TYPE: PRT
<213> ORGANISM: Artificial Sequence
<220> FEATURE:
<223> OTHER INFORMATION: 1-320 aa fragment of Nkx3.2

<400> SEQUENCE: 9

```
Met Ala Val Arg Gly Ala Asn Thr Leu Thr Ser Phe Ser Ile Gln Ala
1               5                   10                  15

Ile Leu Asn Lys Lys Glu Glu Arg Gly Gly Leu Ala Ala Pro Glu Gly
            20                  25                  30

Arg Pro Ala Pro Gly Gly Thr Ala Ala Ser Val Ala Ala Ala Pro Ala
        35                  40                  45

Val Cys Cys Trp Arg Leu Phe Gly Glu Arg Asp Ala Gly Ala Leu Gly
    50                  55                  60

Gly Ala Glu Asp Ser Leu Leu Ala Ser Pro Ala Gly Thr Arg Thr Ala
65                  70                  75                  80

Ala Gly Arg Thr Ala Glu Ser Pro Glu Gly Trp Asp Ser Asp Ser Ala
                85                  90                  95

Leu Ser Glu Glu Asn Glu Ser Arg Arg Arg Cys Ala Asp Ala Arg Gly
            100                 105                 110

Ala Ser Gly Ala Gly Leu Ala Gly Gly Ser Leu Ser Leu Gly Gln Pro
        115                 120                 125

Val Cys Glu Leu Ala Ala Ser Lys Asp Leu Glu Glu Glu Ala Ala Gly
    130                 135                 140

Arg Ser Asp Ser Glu Met Ser Ala Ser Val Ser Gly Asp Arg Ser Pro
145                 150                 155                 160

Arg Thr Glu Asp Asp Gly Val Gly Pro Arg Gly Ala His Val Ser Ala
                165                 170                 175

Leu Cys Ser Gly Ala Gly Gly Gly Gly Ser Gly Pro Ala Gly Val
            180                 185                 190

Ala Glu Glu Glu Glu Pro Ala Ala Pro Lys Pro Arg Lys Lys Arg
        195                 200                 205

Ser Arg Ala Ala Phe Ser His Ala Gln Val Phe Glu Leu Glu Arg Arg
    210                 215                 220

Phe Asn His Gln Arg Tyr Leu Ser Gly Pro Glu Arg Ala Asp Leu Ala
225                 230                 235                 240

Ala Ser Leu Lys Leu Thr Glu Thr Gln Val Lys Ile Trp Phe Gln Asn
                245                 250                 255

Arg Arg Tyr Lys Thr Lys Arg Arg Gln Met Ala Ala Asp Leu Leu Ala
            260                 265                 270

Ser Ala Pro Ala Ala Lys Lys Val Ala Val Lys Val Leu Val Arg Asp
        275                 280                 285

Asp Gln Arg Gln Tyr Leu Pro Gly Glu Val Leu Arg Pro Pro Ser Leu
    290                 295                 300
```

Leu Pro Leu Gln Pro Ser Tyr Tyr Tyr Pro Tyr Tyr Cys Leu Pro Gly
305                 310                 315                 320

<210> SEQ ID NO 10
<211> LENGTH: 307
<212> TYPE: PRT
<213> ORGANISM: Artificial Sequence
<220> FEATURE:
<223> OTHER INFORMATION: 1-307 aa fragment of Nkx3.2

<400> SEQUENCE: 10

Met Ala Val Arg Gly Ala Asn Thr Leu Thr Ser Phe Ser Ile Gln Ala
1               5                   10                  15

Ile Leu Asn Lys Lys Glu Arg Gly Gly Leu Ala Ala Pro Glu Gly
            20                  25                  30

Arg Pro Ala Pro Gly Gly Thr Ala Ala Ser Val Ala Ala Ala Pro Ala
            35                  40                  45

Val Cys Cys Trp Arg Leu Phe Gly Glu Arg Asp Ala Gly Ala Leu Gly
    50                  55                  60

Gly Ala Glu Asp Ser Leu Leu Ala Ser Pro Ala Gly Thr Arg Thr Ala
65                  70                  75                  80

Ala Gly Arg Thr Ala Glu Ser Pro Glu Gly Trp Asp Ser Asp Ser Ala
                85                  90                  95

Leu Ser Glu Glu Asn Glu Ser Arg Arg Cys Ala Asp Ala Arg Gly
            100                 105                 110

Ala Ser Gly Ala Gly Leu Ala Gly Gly Ser Leu Ser Leu Gly Gln Pro
        115                 120                 125

Val Cys Glu Leu Ala Ala Ser Lys Asp Leu Glu Glu Glu Ala Ala Gly
    130                 135                 140

Arg Ser Asp Ser Glu Met Ser Ala Ser Val Ser Gly Arg Ser Pro
145                 150                 155                 160

Arg Thr Glu Asp Asp Gly Val Gly Pro Arg Gly Ala His Val Ser Ala
                165                 170                 175

Leu Cys Ser Gly Ala Gly Gly Gly Gly Ser Gly Pro Ala Gly Val
            180                 185                 190

Ala Glu Glu Glu Glu Pro Ala Ala Pro Lys Pro Arg Lys Lys Arg
        195                 200                 205

Ser Arg Ala Ala Phe Ser His Ala Gln Val Phe Glu Leu Glu Arg Arg
    210                 215                 220

Phe Asn His Gln Arg Tyr Leu Ser Gly Pro Glu Arg Ala Asp Leu Ala
225                 230                 235                 240

Ala Ser Leu Lys Leu Thr Glu Thr Gln Val Lys Ile Trp Phe Gln Asn
                245                 250                 255

Arg Arg Tyr Lys Thr Lys Arg Arg Gln Met Ala Ala Asp Leu Leu Ala
            260                 265                 270

Ser Ala Pro Ala Ala Lys Lys Val Ala Val Lys Val Leu Val Arg Asp
        275                 280                 285

Asp Gln Arg Gln Tyr Leu Pro Gly Glu Val Leu Arg Pro Pro Ser Leu
    290                 295                 300

Leu Pro Leu
305

<210> SEQ ID NO 11
<211> LENGTH: 292
<212> TYPE: PRT
<213> ORGANISM: Artificial Sequence
<220> FEATURE:
<223> OTHER INFORMATION: 42-333 aa fragment of Nkx3.2

<400> SEQUENCE: 11

```
Ser Val Ala Ala Ala Pro Ala Val Cys Cys Trp Arg Leu Phe Gly Glu
1               5                   10                  15

Arg Asp Ala Gly Ala Leu Gly Gly Ala Glu Asp Ser Leu Leu Ala Ser
            20                  25                  30

Pro Ala Gly Thr Arg Thr Ala Ala Gly Arg Thr Ala Glu Ser Pro Glu
        35                  40                  45

Gly Trp Asp Ser Asp Ser Ala Leu Ser Glu Glu Asn Glu Ser Arg Arg
50                  55                  60

Arg Cys Ala Asp Ala Arg Gly Ala Ser Gly Ala Gly Leu Ala Gly Gly
65                  70                  75                  80

Ser Leu Ser Leu Gly Gln Pro Val Cys Glu Leu Ala Ala Ser Lys Asp
                85                  90                  95

Leu Glu Glu Glu Ala Ala Gly Arg Ser Asp Ser Glu Met Ser Ala Ser
            100                 105                 110

Val Ser Gly Asp Arg Ser Pro Arg Thr Glu Asp Asp Gly Val Gly Pro
        115                 120                 125

Arg Gly Ala His Val Ser Ala Leu Cys Ser Gly Ala Gly Gly Gly Gly
130                 135                 140

Gly Ser Gly Pro Ala Gly Val Ala Glu Glu Glu Glu Pro Ala Ala
145                 150                 155                 160

Pro Lys Pro Arg Lys Lys Arg Ser Arg Ala Ala Phe Ser His Ala Gln
                165                 170                 175

Val Phe Glu Leu Glu Arg Arg Phe Asn His Gln Arg Tyr Leu Ser Gly
            180                 185                 190

Pro Glu Arg Ala Asp Leu Ala Ala Ser Leu Lys Leu Thr Glu Thr Gln
        195                 200                 205

Val Lys Ile Trp Phe Gln Asn Arg Arg Tyr Lys Thr Lys Arg Arg Gln
210                 215                 220

Met Ala Ala Asp Leu Leu Ala Ser Ala Pro Ala Ala Lys Lys Val Ala
225                 230                 235                 240

Val Lys Val Leu Val Arg Asp Asp Gln Arg Gln Tyr Leu Pro Gly Glu
                245                 250                 255

Val Leu Arg Pro Pro Ser Leu Leu Pro Leu Gln Pro Ser Tyr Tyr Tyr
            260                 265                 270

Pro Tyr Tyr Cys Leu Pro Gly Trp Ala Leu Ser Thr Cys Ala Ala Ala
        275                 280                 285

Ala Gly Thr Gln
    290
```

<210> SEQ ID NO 12
<211> LENGTH: 235
<212> TYPE: PRT
<213> ORGANISM: Artificial Sequence
<220> FEATURE:
<223> OTHER INFORMATION: 99-333 aa fragment of Nkx3.2

<400> SEQUENCE: 12

```
Glu Glu Asn Glu Ser Arg Arg Arg Cys Ala Asp Ala Arg Gly Ala Ser
1               5                   10                  15

Gly Ala Gly Leu Ala Gly Gly Ser Leu Ser Leu Gly Gln Pro Val Cys
            20                  25                  30

Glu Leu Ala Ala Ser Lys Asp Leu Glu Glu Glu Ala Ala Gly Arg Ser
```

```
            35                  40                  45
Asp Ser Glu Met Ser Ala Ser Val Ser Gly Asp Arg Ser Pro Arg Thr
 50                  55                  60
Glu Asp Asp Gly Val Gly Pro Arg Gly Ala His Val Ser Ala Leu Cys
 65                  70                  75                  80
Ser Gly Ala Gly Gly Gly Gly Ser Gly Pro Ala Gly Val Ala Glu
                 85                  90                  95
Glu Glu Glu Pro Ala Ala Pro Lys Pro Arg Lys Lys Arg Ser Arg
                100                 105                 110
Ala Ala Phe Ser His Ala Gln Val Phe Glu Leu Glu Arg Arg Phe Asn
            115                 120                 125
His Gln Arg Tyr Leu Ser Gly Pro Glu Arg Ala Asp Leu Ala Ala Ser
            130                 135                 140
Leu Lys Leu Thr Glu Thr Gln Val Lys Ile Trp Phe Gln Asn Arg Arg
145                 150                 155                 160
Tyr Lys Thr Lys Arg Arg Gln Met Ala Ala Asp Leu Leu Ala Ser Ala
                165                 170                 175
Pro Ala Ala Lys Lys Val Ala Val Lys Val Leu Val Arg Asp Asp Gln
                180                 185                 190
Arg Gln Tyr Leu Pro Gly Glu Val Leu Arg Pro Ser Leu Leu Pro
            195                 200                 205
Leu Gln Pro Ser Tyr Tyr Tyr Pro Tyr Tyr Cys Leu Pro Gly Trp Ala
210                 215                 220
Leu Ser Thr Cys Ala Ala Ala Gly Thr Gln
225                 230                 235

<210> SEQ ID NO 13
<211> LENGTH: 222
<212> TYPE: PRT
<213> ORGANISM: Artificial Sequence
<220> FEATURE:
<223> OTHER INFORMATION: 112-333 aa fragment of Nkx3.2

<400> SEQUENCE: 13

Gly Ala Ser Gly Ala Gly Leu Ala Gly Gly Ser Leu Ser Leu Gly Gln
 1               5                  10                  15
Pro Val Cys Glu Leu Ala Ala Ser Lys Asp Leu Glu Glu Glu Ala Ala
                20                  25                  30
Gly Arg Ser Asp Ser Glu Met Ser Ala Ser Val Ser Gly Asp Arg Ser
            35                  40                  45
Pro Arg Thr Glu Asp Asp Gly Val Gly Pro Arg Gly Ala His Val Ser
 50                  55                  60
Ala Leu Cys Ser Gly Ala Gly Gly Gly Gly Ser Gly Pro Ala Gly
 65                  70                  75                  80
Val Ala Glu Glu Glu Glu Pro Ala Ala Pro Lys Pro Arg Lys Lys
                 85                  90                  95
Arg Ser Arg Ala Ala Phe Ser His Ala Gln Val Phe Glu Leu Glu Arg
                100                 105                 110
Arg Phe Asn His Gln Arg Tyr Leu Ser Gly Pro Glu Arg Ala Asp Leu
            115                 120                 125
Ala Ala Ser Leu Lys Leu Thr Glu Thr Gln Val Lys Ile Trp Phe Gln
            130                 135                 140
Asn Arg Arg Tyr Lys Thr Lys Arg Arg Gln Met Ala Ala Asp Leu Leu
145                 150                 155                 160
Ala Ser Ala Pro Ala Ala Lys Lys Val Ala Val Lys Val Leu Val Arg
```

```
                    165                 170                 175
Asp Asp Gln Arg Gln Tyr Leu Pro Gly Glu Val Leu Arg Pro Pro Ser
            180                 185                 190

Leu Leu Pro Leu Gln Pro Ser Tyr Tyr Pro Tyr Tyr Cys Leu Pro
        195                 200                 205

Gly Trp Ala Leu Ser Thr Cys Ala Ala Ala Gly Thr Gln
    210                 215                 220

<210> SEQ ID NO 14
<211> LENGTH: 211
<212> TYPE: PRT
<213> ORGANISM: Artificial Sequence
<220> FEATURE:
<223> OTHER INFORMATION: 123-333 aa fragment of Nkx3.2

<400> SEQUENCE: 14

Leu Ser Leu Gly Gln Pro Val Cys Glu Leu Ala Ala Ser Lys Asp Leu
1               5                   10                  15

Glu Glu Glu Ala Ala Gly Arg Ser Asp Ser Glu Met Ser Ala Ser Val
            20                  25                  30

Ser Gly Asp Arg Ser Pro Arg Thr Glu Asp Asp Gly Val Gly Pro Arg
        35                  40                  45

Gly Ala His Val Ser Ala Leu Cys Ser Gly Ala Gly Gly Gly Gly Gly
    50                  55                  60

Ser Gly Pro Ala Gly Val Ala Glu Glu Glu Glu Pro Ala Ala Pro
65                  70                  75                  80

Lys Pro Arg Lys Lys Arg Ser Arg Ala Ala Phe Ser His Ala Gln Val
                85                  90                  95

Phe Glu Leu Glu Arg Arg Phe Asn His Gln Arg Tyr Leu Ser Gly Pro
            100                 105                 110

Glu Arg Ala Asp Leu Ala Ala Ser Leu Lys Leu Thr Glu Thr Gln Val
        115                 120                 125

Lys Ile Trp Phe Gln Asn Arg Arg Tyr Lys Thr Lys Arg Arg Gln Met
    130                 135                 140

Ala Ala Asp Leu Leu Ala Ser Ala Pro Ala Ala Lys Lys Val Ala Val
145                 150                 155                 160

Lys Val Leu Val Arg Asp Asp Gln Arg Gln Tyr Leu Pro Gly Glu Val
                165                 170                 175

Leu Arg Pro Pro Ser Leu Leu Pro Leu Gln Pro Ser Tyr Tyr Tyr Pro
            180                 185                 190

Tyr Tyr Cys Leu Pro Gly Trp Ala Leu Ser Thr Cys Ala Ala Ala Ala
        195                 200                 205

Gly Thr Gln
    210

<210> SEQ ID NO 15
<211> LENGTH: 232
<212> TYPE: PRT
<213> ORGANISM: Artificial Sequence
<220> FEATURE:
<223> OTHER INFORMATION: 99-330 aa fragment of Nkx3.2

<400> SEQUENCE: 15

Glu Glu Asn Glu Ser Arg Arg Arg Cys Ala Asp Ala Arg Gly Ala Ser
1               5                   10                  15

Gly Ala Gly Leu Ala Gly Gly Ser Leu Ser Leu Gly Gln Pro Val Cys
            20                  25                  30
```

Glu Leu Ala Ala Ser Lys Asp Leu Glu Glu Ala Ala Gly Arg Ser
            35                  40                  45

Asp Ser Glu Met Ser Ala Ser Val Ser Gly Asp Arg Ser Pro Arg Thr
 50                  55                  60

Glu Asp Asp Gly Val Gly Pro Arg Gly Ala His Val Ser Ala Leu Cys
 65                  70                  75                  80

Ser Gly Ala Gly Gly Gly Gly Ser Gly Pro Ala Gly Val Ala Glu
                85                  90                  95

Glu Glu Glu Glu Pro Ala Ala Pro Lys Pro Arg Lys Lys Arg Ser Arg
                100                 105                 110

Ala Ala Phe Ser His Ala Gln Val Phe Glu Leu Glu Arg Arg Phe Asn
            115                 120                 125

His Gln Arg Tyr Leu Ser Gly Pro Glu Arg Ala Asp Leu Ala Ala Ser
130                 135                 140

Leu Lys Leu Thr Glu Thr Gln Val Lys Ile Trp Phe Gln Asn Arg Arg
145                 150                 155                 160

Tyr Lys Thr Lys Arg Arg Gln Met Ala Ala Asp Leu Leu Ala Ser Ala
                165                 170                 175

Pro Ala Ala Lys Lys Val Ala Val Lys Val Leu Val Arg Asp Asp Gln
                180                 185                 190

Arg Gln Tyr Leu Pro Gly Glu Val Leu Arg Pro Pro Ser Leu Leu Pro
            195                 200                 205

Leu Gln Pro Ser Tyr Tyr Tyr Pro Tyr Tyr Cys Leu Pro Gly Trp Ala
            210                 215                 220

Leu Ser Thr Cys Ala Ala Ala
225                 230

<210> SEQ ID NO 16
<211> LENGTH: 229
<212> TYPE: PRT
<213> ORGANISM: Artificial Sequence
<220> FEATURE:
<223> OTHER INFORMATION: 99-327 aa fragment of Nkx3.2

<400> SEQUENCE: 16

Glu Glu Asn Glu Ser Arg Arg Arg Cys Ala Asp Ala Arg Gly Ala Ser
 1               5                   10                  15

Gly Ala Gly Leu Ala Gly Gly Ser Leu Ser Leu Gly Gln Pro Val Cys
                20                  25                  30

Glu Leu Ala Ala Ser Lys Asp Leu Glu Glu Ala Ala Gly Arg Ser
            35                  40                  45

Asp Ser Glu Met Ser Ala Ser Val Ser Gly Asp Arg Ser Pro Arg Thr
 50                  55                  60

Glu Asp Asp Gly Val Gly Pro Arg Gly Ala His Val Ser Ala Leu Cys
 65                  70                  75                  80

Ser Gly Ala Gly Gly Gly Gly Ser Gly Pro Ala Gly Val Ala Glu
                85                  90                  95

Glu Glu Glu Glu Pro Ala Ala Pro Lys Pro Arg Lys Lys Arg Ser Arg
                100                 105                 110

Ala Ala Phe Ser His Ala Gln Val Phe Glu Leu Glu Arg Arg Phe Asn
            115                 120                 125

His Gln Arg Tyr Leu Ser Gly Pro Glu Arg Ala Asp Leu Ala Ala Ser
130                 135                 140

Leu Lys Leu Thr Glu Thr Gln Val Lys Ile Trp Phe Gln Asn Arg Arg
145                 150                 155                 160

Tyr Lys Thr Lys Arg Arg Gln Met Ala Ala Asp Leu Leu Ala Ser Ala
            165                 170                 175

Pro Ala Ala Lys Lys Val Ala Val Lys Val Leu Val Arg Asp Asp Gln
            180                 185                 190

Arg Gln Tyr Leu Pro Gly Glu Val Leu Arg Pro Pro Ser Leu Leu Pro
        195                 200                 205

Leu Gln Pro Ser Tyr Tyr Tyr Pro Tyr Tyr Cys Leu Pro Gly Trp Ala
    210                 215                 220

Leu Ser Thr Cys Ala
225

<210> SEQ ID NO 17
<211> LENGTH: 222
<212> TYPE: PRT
<213> ORGANISM: Artificial Sequence
<220> FEATURE:
<223> OTHER INFORMATION: 99-320 aa fragment of Nkx3.2

<400> SEQUENCE: 17

Glu Glu Asn Glu Ser Arg Arg Arg Cys Ala Asp Ala Arg Gly Ala Ser
1               5                   10                  15

Gly Ala Gly Leu Ala Gly Gly Ser Leu Ser Leu Gly Gln Pro Val Cys
            20                  25                  30

Glu Leu Ala Ala Ser Lys Asp Leu Glu Glu Glu Ala Ala Gly Arg Ser
        35                  40                  45

Asp Ser Glu Met Ser Ala Ser Val Ser Gly Asp Arg Ser Pro Arg Thr
    50                  55                  60

Glu Asp Asp Gly Val Gly Pro Arg Gly Ala His Val Ser Ala Leu Cys
65                  70                  75                  80

Ser Gly Ala Gly Gly Gly Gly Ser Gly Pro Ala Gly Val Ala Glu
            85                  90                  95

Glu Glu Glu Glu Pro Ala Ala Pro Lys Pro Arg Lys Lys Arg Ser Arg
            100                 105                 110

Ala Ala Phe Ser His Ala Gln Val Phe Glu Leu Glu Arg Arg Phe Asn
        115                 120                 125

His Gln Arg Tyr Leu Ser Gly Pro Glu Arg Ala Asp Leu Ala Ala Ser
    130                 135                 140

Leu Lys Leu Thr Glu Thr Gln Val Lys Ile Trp Phe Gln Asn Arg Arg
145                 150                 155                 160

Tyr Lys Thr Lys Arg Arg Gln Met Ala Ala Asp Leu Leu Ala Ser Ala
            165                 170                 175

Pro Ala Ala Lys Lys Val Ala Val Lys Val Leu Val Arg Asp Asp Gln
            180                 185                 190

Arg Gln Tyr Leu Pro Gly Glu Val Leu Arg Pro Pro Ser Leu Leu Pro
        195                 200                 205

Leu Gln Pro Ser Tyr Tyr Tyr Pro Tyr Tyr Cys Leu Pro Gly
    210                 215                 220

<210> SEQ ID NO 18
<211> LENGTH: 223
<212> TYPE: PRT
<213> ORGANISM: Artificial Sequence
<220> FEATURE:
<223> OTHER INFORMATION: 105-327 aa fragment of Nkx3.2

<400> SEQUENCE: 18

Arg Arg Cys Ala Asp Ala Arg Gly Ala Ser Gly Ala Gly Leu Ala Gly
1               5                   10                  15

Gly Ser Leu Ser Leu Gly Gln Pro Val Cys Glu Leu Ala Ala Ser Lys
            20                  25                  30

Asp Leu Glu Glu Ala Ala Gly Arg Ser Asp Ser Glu Met Ser Ala
        35                  40                  45

Ser Val Ser Gly Asp Arg Ser Pro Arg Thr Glu Asp Asp Gly Val Gly
 50                  55                  60

Pro Arg Gly Ala His Val Ser Ala Leu Cys Ser Gly Ala Gly Gly
65                   70                  75                  80

Gly Gly Ser Gly Pro Ala Gly Val Ala Glu Glu Glu Glu Pro Ala
                85                  90                  95

Ala Pro Lys Pro Arg Lys Arg Ser Arg Ala Ala Phe Ser His Ala
            100                 105                 110

Gln Val Phe Glu Leu Glu Arg Arg Phe Asn His Gln Arg Tyr Leu Ser
            115                 120                 125

Gly Pro Glu Arg Ala Asp Leu Ala Ala Ser Leu Lys Leu Thr Glu Thr
 130                 135                 140

Gln Val Lys Ile Trp Phe Gln Asn Arg Arg Tyr Lys Thr Lys Arg Arg
145                 150                 155                 160

Gln Met Ala Ala Asp Leu Leu Ala Ser Ala Pro Ala Ala Lys Lys Val
                165                 170                 175

Ala Val Lys Val Leu Val Arg Asp Asp Gln Arg Gln Tyr Leu Pro Gly
            180                 185                 190

Glu Val Leu Arg Pro Pro Ser Leu Leu Pro Leu Gln Pro Ser Tyr Tyr
            195                 200                 205

Tyr Pro Tyr Tyr Cys Leu Pro Gly Trp Ala Leu Ser Thr Cys Ala
 210                 215                 220

<210> SEQ ID NO 19
<211> LENGTH: 215
<212> TYPE: PRT
<213> ORGANISM: Artificial Sequence
<220> FEATURE:
<223> OTHER INFORMATION: 110-324 aa fragment of Nkx3.2

<400> SEQUENCE: 19

Ala Arg Gly Ala Ser Gly Ala Gly Leu Ala Gly Gly Ser Leu Ser Leu
1               5                   10                  15

Gly Gln Pro Val Cys Glu Leu Ala Ala Ser Lys Asp Leu Glu Glu
            20                  25                  30

Ala Ala Gly Arg Ser Asp Ser Glu Met Ser Ala Ser Val Ser Gly Asp
            35                  40                  45

Arg Ser Pro Arg Thr Glu Asp Asp Gly Val Gly Pro Arg Gly Ala His
 50                  55                  60

Val Ser Ala Leu Cys Ser Gly Ala Gly Gly Gly Gly Ser Gly Pro
65                   70                  75                  80

Ala Gly Val Ala Glu Glu Glu Glu Pro Ala Ala Pro Lys Pro Arg
                85                  90                  95

Lys Lys Arg Ser Arg Ala Ala Phe Ser His Ala Gln Val Phe Glu Leu
            100                 105                 110

Glu Arg Arg Phe Asn His Gln Arg Tyr Leu Ser Gly Pro Glu Arg Ala
            115                 120                 125

Asp Leu Ala Ala Ser Leu Lys Leu Thr Glu Thr Gln Val Lys Ile Trp
 130                 135                 140

Phe Gln Asn Arg Arg Tyr Lys Thr Lys Arg Arg Gln Met Ala Ala Asp
145                 150                 155                 160

```
Leu Leu Ala Ser Ala Pro Ala Ala Lys Lys Val Ala Lys Val Leu
            165                 170                 175

Val Arg Asp Asp Gln Arg Gln Tyr Leu Pro Gly Glu Val Leu Arg Pro
        180                 185                 190

Pro Ser Leu Leu Pro Leu Gln Pro Ser Tyr Tyr Tyr Pro Tyr Tyr Cys
            195                 200                 205

Leu Pro Gly Trp Ala Leu Ser
        210                 215

<210> SEQ ID NO 20
<211> LENGTH: 209
<212> TYPE: PRT
<213> ORGANISM: Artificial Sequence
<220> FEATURE:
<223> OTHER INFORMATION: 112-320 aa fragment of Nkx3.2

<400> SEQUENCE: 20

Gly Ala Ser Gly Ala Gly Leu Ala Gly Gly Ser Leu Ser Leu Gly Gln
1               5                   10                  15

Pro Val Cys Glu Leu Ala Ala Ser Lys Asp Leu Glu Glu Glu Ala Ala
            20                  25                  30

Gly Arg Ser Asp Ser Glu Met Ser Ala Ser Val Ser Gly Asp Arg Ser
        35                  40                  45

Pro Arg Thr Glu Asp Asp Gly Val Gly Pro Arg Gly Ala His Val Ser
    50                  55                  60

Ala Leu Cys Ser Gly Ala Gly Gly Gly Ser Gly Pro Ala Gly
65                  70                  75                  80

Val Ala Glu Glu Glu Glu Pro Ala Ala Pro Lys Pro Arg Lys Lys
            85                  90                  95

Arg Ser Arg Ala Ala Phe Ser His Ala Gln Val Phe Glu Leu Glu Arg
        100                 105                 110

Arg Phe Asn His Gln Arg Tyr Leu Ser Gly Pro Glu Arg Ala Asp Leu
    115                 120                 125

Ala Ala Ser Leu Lys Leu Thr Glu Thr Gln Val Lys Ile Trp Phe Gln
130                 135                 140

Asn Arg Arg Tyr Lys Thr Lys Arg Arg Gln Met Ala Ala Asp Leu Leu
145                 150                 155                 160

Ala Ser Ala Pro Ala Ala Lys Lys Val Ala Val Lys Val Leu Val Arg
            165                 170                 175

Asp Asp Gln Arg Gln Tyr Leu Pro Gly Glu Val Leu Arg Pro Pro Ser
        180                 185                 190

Leu Leu Pro Leu Gln Pro Ser Tyr Tyr Tyr Pro Tyr Tyr Cys Leu Pro
            195                 200                 205

Gly

<210> SEQ ID NO 21
<211> LENGTH: 198
<212> TYPE: PRT
<213> ORGANISM: Artificial Sequence
<220> FEATURE:
<223> OTHER INFORMATION: 123-320 aa fragment of Nkx3.2

<400> SEQUENCE: 21

Leu Ser Leu Gly Gln Pro Val Cys Glu Leu Ala Ala Ser Lys Asp Leu
1               5                   10                  15

Glu Glu Glu Ala Ala Gly Arg Ser Asp Ser Glu Met Ser Ala Ser Val
            20                  25                  30
```

```
Ser Gly Asp Arg Ser Pro Arg Thr Glu Asp Asp Gly Val Gly Pro Arg
        35                  40                  45

Gly Ala His Val Ser Ala Leu Cys Ser Gly Ala Gly Gly Gly Gly Gly
 50                  55                  60

Ser Gly Pro Ala Gly Val Ala Glu Glu Glu Glu Pro Ala Ala Pro
 65                  70                  75                  80

Lys Pro Arg Lys Lys Arg Ser Arg Ala Ala Phe Ser His Ala Gln Val
                85                  90                  95

Phe Glu Leu Glu Arg Arg Phe Asn His Gln Arg Tyr Leu Ser Gly Pro
                100                 105                 110

Glu Arg Ala Asp Leu Ala Ala Ser Leu Lys Leu Thr Glu Thr Gln Val
                115                 120                 125

Lys Ile Trp Phe Gln Asn Arg Arg Tyr Lys Thr Lys Arg Arg Gln Met
130                 135                 140

Ala Ala Asp Leu Leu Ala Ser Ala Pro Ala Ala Lys Lys Val Ala Val
145                 150                 155                 160

Lys Val Leu Val Arg Asp Asp Gln Arg Gln Tyr Leu Pro Gly Glu Val
                165                 170                 175

Leu Arg Pro Pro Ser Leu Leu Pro Leu Gln Pro Ser Tyr Tyr Tyr Pro
                180                 185                 190

Tyr Tyr Cys Leu Pro Gly
            195

<210> SEQ ID NO 22
<211> LENGTH: 191
<212> TYPE: PRT
<213> ORGANISM: Artificial Sequence
<220> FEATURE:
<223> OTHER INFORMATION: 130-320 aa fragment of Nkx3.2

<400> SEQUENCE: 22

Cys Glu Leu Ala Ala Ser Lys Asp Leu Glu Glu Glu Ala Ala Gly Arg
1               5                   10                  15

Ser Asp Ser Glu Met Ser Ala Ser Val Ser Gly Asp Arg Ser Pro Arg
                20                  25                  30

Thr Glu Asp Asp Gly Val Gly Pro Arg Gly Ala His Val Ser Ala Leu
                35                  40                  45

Cys Ser Gly Ala Gly Gly Gly Gly Ser Gly Pro Ala Gly Val Ala
 50                  55                  60

Glu Glu Glu Glu Pro Ala Ala Pro Lys Pro Arg Lys Lys Arg Ser
 65                  70                  75                  80

Arg Ala Ala Phe Ser His Ala Gln Val Phe Glu Leu Glu Arg Arg Phe
                85                  90                  95

Asn His Gln Arg Tyr Leu Ser Gly Pro Glu Arg Ala Asp Leu Ala Ala
                100                 105                 110

Ser Leu Lys Leu Thr Glu Thr Gln Val Lys Ile Trp Phe Gln Asn Arg
                115                 120                 125

Arg Tyr Lys Thr Lys Arg Arg Gln Met Ala Ala Asp Leu Leu Ala Ser
                130                 135                 140

Ala Pro Ala Ala Lys Lys Val Ala Val Lys Val Leu Val Arg Asp Asp
145                 150                 155                 160

Gln Arg Gln Tyr Leu Pro Gly Glu Val Leu Arg Pro Pro Ser Leu Leu
                165                 170                 175

Pro Leu Gln Pro Ser Tyr Tyr Tyr Pro Tyr Tyr Cys Leu Pro Gly
                180                 185                 190
```

<210> SEQ ID NO 23
<211> LENGTH: 171
<212> TYPE: PRT
<213> ORGANISM: Artificial Sequence
<220> FEATURE:
<223> OTHER INFORMATION: 150-320 aa fragment of Nkx3.2

<400> SEQUENCE: 23

```
Met Ser Ala Ser Val Ser Gly Asp Arg Ser Pro Arg Thr Glu Asp Asp
1               5                   10                  15

Gly Val Gly Pro Arg Gly Ala His Val Ser Ala Leu Cys Ser Gly Ala
            20                  25                  30

Gly Gly Gly Gly Ser Gly Pro Ala Gly Val Ala Glu Glu Glu Glu Glu
        35                  40                  45

Glu Pro Ala Ala Pro Lys Pro Arg Lys Lys Arg Ser Arg Ala Ala Phe
50                  55                  60

Ser His Ala Gln Val Phe Glu Leu Glu Arg Arg Phe Asn His Gln Arg
65                  70                  75                  80

Tyr Leu Ser Gly Pro Glu Arg Ala Asp Leu Ala Ala Ser Leu Lys Leu
                85                  90                  95

Thr Glu Thr Gln Val Lys Ile Trp Phe Gln Asn Arg Arg Tyr Lys Thr
            100                 105                 110

Lys Arg Arg Gln Met Ala Ala Asp Leu Leu Ala Ser Ala Pro Ala Ala
        115                 120                 125

Lys Lys Val Ala Val Lys Val Leu Val Arg Asp Asp Gln Arg Gln Tyr
    130                 135                 140

Leu Pro Gly Glu Val Leu Arg Pro Pro Ser Leu Leu Pro Leu Gln Pro
145                 150                 155                 160

Ser Tyr Tyr Tyr Pro Tyr Tyr Cys Leu Pro Gly
                165                 170
```

<210> SEQ ID NO 24
<211> LENGTH: 166
<212> TYPE: PRT
<213> ORGANISM: Artificial Sequence
<220> FEATURE:
<223> OTHER INFORMATION: 153-318 aa fragment of Nkx3.2

<400> SEQUENCE: 24

```
Ser Val Ser Gly Asp Arg Ser Pro Arg Thr Glu Asp Asp Gly Val Gly
1               5                   10                  15

Pro Arg Gly Ala His Val Ser Ala Leu Cys Ser Gly Ala Gly Gly Gly
            20                  25                  30

Gly Gly Ser Gly Pro Ala Gly Val Ala Glu Glu Glu Glu Glu Pro Ala
        35                  40                  45

Ala Pro Lys Pro Arg Lys Lys Arg Ser Arg Ala Ala Phe Ser His Ala
50                  55                  60

Gln Val Phe Glu Leu Glu Arg Arg Phe Asn His Gln Arg Tyr Leu Ser
65                  70                  75                  80

Gly Pro Glu Arg Ala Asp Leu Ala Ala Ser Leu Lys Leu Thr Glu Thr
                85                  90                  95

Gln Val Lys Ile Trp Phe Gln Asn Arg Arg Tyr Lys Thr Lys Arg Arg
            100                 105                 110

Gln Met Ala Ala Asp Leu Leu Ala Ser Ala Pro Ala Ala Lys Lys Val
        115                 120                 125

Ala Val Lys Val Leu Val Arg Asp Asp Gln Arg Gln Tyr Leu Pro Gly
```

```
                130                 135                 140
Glu Val Leu Arg Pro Pro Ser Leu Leu Pro Gln Pro Ser Tyr Tyr
145                 150                 155                 160

Tyr Pro Tyr Tyr Cys Leu
                165

<210> SEQ ID NO 25
<211> LENGTH: 161
<212> TYPE: PRT
<213> ORGANISM: Artificial Sequence
<220> FEATURE:
<223> OTHER INFORMATION: 156-316 aa fragment of Nkx3.2

<400> SEQUENCE: 25

Gly Asp Arg Ser Pro Arg Thr Glu Asp Asp Gly Val Gly Pro Arg Gly
1               5                   10                  15

Ala His Val Ser Ala Leu Cys Ser Gly Ala Gly Gly Gly Gly Gly Ser
                20                  25                  30

Gly Pro Ala Gly Val Ala Glu Glu Glu Glu Pro Ala Ala Pro Lys
            35                  40                  45

Pro Arg Lys Lys Arg Ser Arg Ala Ala Phe Ser His Ala Gln Val Phe
50                  55                  60

Glu Leu Glu Arg Arg Phe Asn His Gln Arg Tyr Leu Ser Gly Pro Glu
65                  70                  75                  80

Arg Ala Asp Leu Ala Ala Ser Leu Lys Leu Thr Glu Thr Gln Val Lys
                85                  90                  95

Ile Trp Phe Gln Asn Arg Arg Tyr Lys Thr Lys Arg Arg Gln Met Ala
            100                 105                 110

Ala Asp Leu Leu Ala Ser Ala Pro Ala Ala Lys Lys Val Ala Val Lys
        115                 120                 125

Val Leu Val Arg Asp Asp Gln Arg Gln Tyr Leu Pro Gly Glu Val Leu
    130                 135                 140

Arg Pro Pro Ser Leu Leu Pro Leu Gln Pro Ser Tyr Tyr Tyr Pro Tyr
145                 150                 155                 160

Tyr

<210> SEQ ID NO 26
<211> LENGTH: 156
<212> TYPE: PRT
<213> ORGANISM: Artificial Sequence
<220> FEATURE:
<223> OTHER INFORMATION: 159-314 aa fragment of Nkx3.2

<400> SEQUENCE: 26

Ser Pro Arg Thr Glu Asp Asp Gly Val Gly Pro Arg Gly Ala His Val
1               5                   10                  15

Ser Ala Leu Cys Ser Gly Ala Gly Gly Gly Gly Ser Gly Pro Ala
                20                  25                  30

Gly Val Ala Glu Glu Glu Glu Pro Ala Ala Pro Lys Pro Arg Lys
            35                  40                  45

Lys Arg Ser Arg Ala Ala Phe Ser His Ala Gln Val Phe Glu Leu Glu
50                  55                  60

Arg Arg Phe Asn His Gln Arg Tyr Leu Ser Gly Pro Glu Arg Ala Asp
65                  70                  75                  80

Leu Ala Ala Ser Leu Lys Leu Thr Glu Thr Gln Val Lys Ile Trp Phe
                85                  90                  95

Gln Asn Arg Arg Tyr Lys Thr Lys Arg Arg Gln Met Ala Ala Asp Leu
```

```
                    100                 105                 110
Leu Ala Ser Ala Pro Ala Ala Lys Lys Val Ala Lys Val Leu Val
                115                 120                 125

Arg Asp Asp Gln Arg Gln Tyr Leu Pro Gly Glu Val Leu Arg Pro Pro
            130                 135                 140

Ser Leu Leu Pro Leu Gln Pro Ser Tyr Tyr Tyr Pro
145                 150                 155

<210> SEQ ID NO 27
<211> LENGTH: 151
<212> TYPE: PRT
<213> ORGANISM: Artificial Sequence
<220> FEATURE:
<223> OTHER INFORMATION: 162-312 polypeptide fragment of Nkx3.2

<400> SEQUENCE: 27

Thr Glu Asp Asp Gly Val Gly Pro Arg Gly Ala His Val Ser Ala Leu
1               5                   10                  15

Cys Ser Gly Ala Gly Gly Gly Gly Ser Gly Pro Ala Gly Val Ala
                20                  25                  30

Glu Glu Glu Glu Glu Pro Ala Ala Pro Lys Pro Arg Lys Lys Arg Ser
            35                  40                  45

Arg Ala Ala Phe Ser His Ala Gln Val Phe Glu Leu Glu Arg Arg Phe
        50                  55                  60

Asn His Gln Arg Tyr Leu Ser Gly Pro Glu Arg Ala Asp Leu Ala Ala
65                  70                  75                  80

Ser Leu Lys Leu Thr Glu Thr Gln Val Lys Ile Trp Phe Gln Asn Arg
                85                  90                  95

Arg Tyr Lys Thr Lys Arg Arg Gln Met Ala Ala Asp Leu Leu Ala Ser
            100                 105                 110

Ala Pro Ala Ala Lys Lys Val Ala Lys Val Leu Val Arg Asp Asp
        115                 120                 125

Gln Arg Gln Tyr Leu Pro Gly Glu Val Leu Arg Pro Pro Ser Leu Leu
    130                 135                 140

Pro Leu Gln Pro Ser Tyr Tyr
145                 150

<210> SEQ ID NO 28
<211> LENGTH: 146
<212> TYPE: PRT
<213> ORGANISM: Artificial Sequence
<220> FEATURE:
<223> OTHER INFORMATION: 165-310 polypeptide fragment of Nkx3.2

<400> SEQUENCE: 28

Asp Gly Val Gly Pro Arg Gly Ala His Val Ser Ala Leu Cys Ser Gly
1               5                   10                  15

Ala Gly Gly Gly Gly Ser Gly Pro Ala Gly Val Ala Glu Glu Glu
                20                  25                  30

Glu Glu Pro Ala Ala Pro Lys Pro Arg Lys Lys Arg Ser Arg Ala Ala
            35                  40                  45

Phe Ser His Ala Gln Val Phe Glu Leu Glu Arg Arg Phe Asn His Gln
        50                  55                  60

Arg Tyr Leu Ser Gly Pro Glu Arg Ala Asp Leu Ala Ala Ser Leu Lys
65                  70                  75                  80

Leu Thr Glu Thr Gln Val Lys Ile Trp Phe Gln Asn Arg Arg Tyr Lys
                85                  90                  95
```

```
Thr Lys Arg Arg Gln Met Ala Ala Asp Leu Leu Ala Ser Ala Pro Ala
            100                 105                 110

Ala Lys Lys Val Ala Val Lys Val Leu Val Arg Asp Asp Gln Arg Gln
            115                 120                 125

Tyr Leu Pro Gly Glu Val Leu Arg Pro Pro Ser Leu Leu Pro Leu Gln
            130                 135                 140

Pro Ser
145
```